United States Patent
Carrasco et al.

(10) Patent No.: US 7,303,740 B2
(45) Date of Patent: Dec. 4, 2007

(54) METHODS FOR THE DIAGNOSIS AND TREATMENT OF BREAST CANCER

(75) Inventors: Nancy Carrasco, New York, NY (US); Orsolya Dohan, Bronx, NY (US); Uygar H. Tazebay, Ankara (TR); Irene L. Wapnir, Stanford, CA (US)

(73) Assignees: Albert Einstein College of Medicine of Yeshiva University, Bronx, NY (US); University of Medicine and Dentistry of New Jersey, Newark, NJ (US)

( * ) Notice: Subject to any disclaimer, the term of this patent is extended or adjusted under 35 U.S.C. 154(b) by 459 days.

(21) Appl. No.: 10/961,615

(22) Filed: Oct. 8, 2004

(65) Prior Publication Data
US 2006/0014160 A1    Jan. 19, 2006

Related U.S. Application Data

(62) Division of application No. 09/519,959, filed on Mar. 7, 2000, now Pat. No. 6,821,725.

(51) Int. Cl.
```
G01N 33/50    (2006.01)
G01N 33/574   (2006.01)
C12Q 1/68     (2006.01)
A61K 49/00    (2006.01)
A61K 51/10    (2006.01)
A61K 49/04    (2006.01)
```
(52) U.S. Cl. .......................... 424/9.2; 435/6; 435/7.23; 436/501; 436/63; 436/64

(58) Field of Classification Search ..................... None
See application file for complete search history.

(56) References Cited

OTHER PUBLICATIONS

Wapnir et al, J Clin Endocrinol Metab, Apr. 2003, vol. 88, pp. 1880-1888.*
Vayre et al, European Journal of Endocrinology, 1998, vol. 141, pp. 382-386.*
Levy et al (Journal of Bioenergetics and Biomembranes, 1998, vol. 30, pp 195-206).*
Spitweg et al (Journal of Clinical Endocrinology and Metabolism, 1998, vol. 83, pp. 1746-1751).*
Riedel, C., et al., 2001, "Journey of the iodide transporter NIS: from its molecular identification to its clinical role in cancer," Trends in Biochemical Sciences, vol. 26, No. 8, pp. 490-496.
Tazebay, UH, et al., 2000, "The mammary gland iodide transporter is expressed during lactation and in breast cancer," Nauture Medicine, vol. 6, pp. 871-878.
Socolow, EL et al, 1967, "Metabolism of 99m-pertechnetate by the thyroid gland of the rat," Endocrinology, vol. 80, pp. 337-344.
Dai, G. et al. Rattus norvegicus thyroid sodium/iodide symporter NIS mRNA, complete cds. Database NCBI Accession No. U60282, Jul. 2, 1996.
Dai, G. et al. Na/I symporter, Database NCBI Accession No. 2204393A, Oct. 20, 1996.

Smanik, P.A. et al. "Cloning of the Human Sodium Iodide Symporter," Biochemical and Biophysical Research Communications 226, 339-345 (1996).
Cancroft and Goldsmith, (99m)Tc-pertechnetate scintigraphy as an aid in the diagnosis of breast masses. Radiology, 106(2):441-44, Feb. 1973.
Carrasco, N., Iodide transport in the thyroid gland. Biochim. Biophys. Acta., 1154(1):65-82, Jun. 1993.
Caturegli et al., Hypothyroidism in transgenic mice expressing IFN-gamma in the thryoid. Proc. Natl. Acad. Sci. USA, 97(4):1719-24, Feb. 15, 2000.
Dai et al., Cloning and characterization of the thyroid iodide transporter. Nature, 379:458-60, Feb. 1, 1996.
Deleu et al., Characterization of autonomous thyroid adenoma: metabolism, gene expression, and pathology. Thyroid, 10(2):131-40, Feb. 2000.
Eng et al., Escape from the acute Wolff-Chaikoff effect is associated with a decrease in thyroid sodium/iodide symporter messenger ribonucleic acid and protein. Endocrinology, 140(8):3404-10, Aug. 1999.
Eskandari et al., Thyroid Na+/I- symporter: mechanism, stoichiometry, and specificity. J. Biol. Chem., 272(43):27,230-238, Oct. 24, 1997.
Eskin, B.A., Iodine and mammary cancer. Advances in Experimental Medicine and Biology, 91:293-304, 1977.
Eskin et al., Human breast uptake of radioactive iodine. Obstetrics and Gynecology, 44(3):398-402, Sep. 1974.
Filetti et al., Sodium/iodide symporter: a key transport system in thyroid cancer cell metabolism. Eur. J. Endocrinol., 141(5):443-57, Nov. 1999.
Jhiang et al., An immunohistochemical study of Na+/I- symporter in human thyroid tissues and salivary gland tissues. Endocrinology, 139(10):4416-19, Oct. 1998.
Kaminsky et al., Na(+)—I(-) symport activity is present in membrane vesicles from thyrotropin-deprived non-I(-)-transport culture thyroid cells. Proc. Natl. Acad. Sci. USA, 91:.789-93, Apr. 1994.
Kaminsky et al., The Na+/I- symporter of the thyroid gland. In Molecular Biology and Function of Carrier Proteins (New York: The Rockefeller University Press, 1993), chap. 20, 251-62.
Kaminsky et al., Inhibition of the Na+/I- symporter by harmaline and 3-amino-1-methyl-5H-pyrido(4,3-b)indole acetate in thyroid cells and membrane vesicles. Eur. J. Biochem., 200(1):203-07, Aug. 1991.
Kilbane et al., Tissue iodine content and serum-mediated (125)I uptake-blocking activity in breast cancer. JCEM, 85(3):1-6, 2000.
Levy et al., N-linked glycosylation of the tyroid Na+/I- symporter (NIS). J. Biol. Chem., 273(35):22,657-663, Aug. 28, 1998.

(Continued)

*Primary Examiner*—Karen A. Canella
(74) *Attorney, Agent, or Firm*—Amster, Rothstein and Ebenstein LLP

(57) ABSTRACT

The present invention provides a method for diagnosing breast cancer in a subject. The present invention also provides a method for treating breast cancer in a subject. Finally, the present invention provides a method for assessing the efficacy of breast cancer therapy in a subject who has undergone or is undergoing treatment for breast cancer.

7 Claims, 7 Drawing Sheets-

OTHER PUBLICATIONS

Levy et al., Identification of a structural requirement for thyroid Na+/I- symporter (NIS) function from analysis of a mutation that causes human congenital hypothyroidism. FEBS Lett., 429(1):36-40, Jun. 1998.

Levy et al., The Na+/I- symporter (NIS): recent advances. J. Bioenergy. Biomembr., 30(2):195-206, Apr. 1998.

Levy et al., Characterization of the thyroid Na+/I- symporter with an anti-COOH terminus antibody. Proc. Natl. Acad. Sci. USA, 94:5568-73, May 1997.

Lyttle et al., Peroxidase activity and iodide uptake in hormone-responsive and hormone-independent GR mouse mammary tumors. J. Natl. Cancer Inst., 62(4):1031-34, Apr. 1979.

Ohno et al., The paired-domain transcription factor Pax8 binds to the upstream enhancer of the rat sodium/iodide symporter gene and participates in both thyroid-specific and cyclic-AMP-dependent transcription. Mol.. Cell. Biol., 19(3):2051-60, Mar. 1999.

Saito et al., Increased expression of the sodium/iodide symporter in papillary thyroid carcinomas. J. Clin. Invest., 101(7)1296-1300, Apr. 1998.

Shimura et al., Iodide uptake and experimental (131)I therapy in transplanted undifferentiated thyroid cancer cells expressing the Na+I- symporter gene. Endocrinology, 138(10):4493-96, Oct. 1997.

Smanik et al., Expression, exon-intron organization, and chromosome mapping of the human sodium iodide symporter. Endocrinology, 138(8):3555-58, Aug. 1997.

Spitzweg et al., Prostate-specific antigen (PSA) promoter-driven androgen-inducible expression of sodium iodide symporter in prostate cancer cell lines. Cancer Research, 59:2136-41, May 1, 1999.

Spitzweg et al., Analysis of human sodium iodide symporter gene expression in extrathyroidal tissues and cloning of its complementary deoxyribonucleic acids from salivary gland, mammary gland, ang gastric mucosa. JCEM, 83(5):1746-51, May 1998.

Thorpe, S.M., Increased uptake of iodide by hormone-responsive compared to hormone-independent mammary tumors in GR mice. Int. J. Cancer, 18:345-50, Sep. 1976.

Thorpe and Briand, The ability to concentrate iodide as a marker of hormone dependence in GR mouse mammary tumors. Intl. J. Cancer, 34(1):127-31, Jul. 1984.

Uyttersprot et al., Moderate doses of iodide in vivo inhibit cell proliferation and the expression of thyroperoxidase and Na+/I- symporter mRNAs in dog thyroid. Mol. Cell. Endocrinol., 131(2):195-203, Aug. 1997.

Vilijn and Carrasco, Expression of the thyroid sodium/iodide symporter in Xenopus laevis oocytes. J. Biol. Chem., 264(20):11,901-903, Jul. 1989.

* cited by examiner

SEQUENCE LISTING

<160> NUMBER OF SEQ ID NOS: 3

<210> SEQ ID NO 1
<211> LENGTH: 16
<212> TYPE: PRT
<213> ORGANISM: Homo sapiens

<400> SEQUENCE: 1

Lys Glu Leu Glu Gly Ala Gly Ser Trp Thr Pro Cys Val Gly His Asp
1               5                   10                  15

<210> SEQ ID NO 2
<211> LENGTH: 13

```
<212> TYPE: PRT
<213> ORGANISM: Homo sapiens

<400> SEQUENCE: 2

Gly His Asp Gly Gly Arg Asp Gln Gln Glu Thr Asn Leu
1               5                   10

<210> SEQ ID NO 3
<211> LENGTH: 14
<212> TYPE: PRT
<213> ORGANISM: Homo sapiens

<400> SEQUENCE: 3

Asn Glu Asp Leu Leu Phe Phe Leu Gly Gln Lys Glu Leu Glu
1               5                   10
```

METHODS FOR THE DIAGNOSIS AND TREATMENT OF BREAST CANCER

CROSS-REFERENCE TO RELATED APPLICATION

This application is a divisional of U.S. patent application Ser. No. 09/519,959, filed Mar. 7, 2000, now U.S. Pat. No. 6,821,725, the content of which is incorporated by reference in its entirety.

STATEMENT OF GOVERNMENT INTEREST

This invention was made with government support under NIH Grant Nos. DK-07218, R29CA70897, R01CA75503, 5-P30-CA13330-26, and DK-41544. As such, the United States government has certain rights in this invention.

BACKGROUND OF THE INVENTION

Breast cancer is the most common malignancy among women, and has one of the highest fatality rates of all cancers affecting females. In fact, breast cancer remains the leading cause of cancer deaths in women aged 20-59 (Greenlee et al., 2000).

Most breast cancers appear as a slowly growing, painless mass. There are a number of physical signs which might suggest the presence of breast cancer, and these may be discovered through a breast examination. Mammography, xerography, and termography are other established methods of detecting malignant breast masses (Cancroft and Goldsmith, 1973). Breast cancer metastasizes by direct extension, and via the lymphatics and the blood stream. Distant spread of the disease may be confirmed by lymph node biopsy, by x-ray surveys of skeleton and chest, and, when appropriate, by liver and bone scans using radioisotopes. Nevertheless, while history, physical examination, and mammography may strongly suggest breast cancer, a diagnosis can only be made by microscopic examination of tissue removed by excisional biopsy or by aspiration cytology or biopsy. At present, then, there is no means of diagnosing breast cancer in a patient without necessitating the removal of tissue.

Regarding treatment, breast cancer therapy depends mainly on the extent of the disease and the patient's age. There are a number of methods currently used to treat breast cancer, including surgery, radiotherapy, hormone therapy, and chemotherapy. Successful cancer therapy is directed to the primary tumor and to any metastases, whether clinically apparent or microscopic. Because breast tumors may be cured with combined modality therapy, each of the above methods may be used alone, or in conjunction with one or more other therapies. Thus, local and regional therapy, surgery, or radiotherapy is often integrated with systemic therapy (e.g., chemotherapy). Adjunctive chemotherapy, in particular, has a definite role in the treatment of patients with breast cancer and axillary lymph node involvement.

When there is no evidence that cancer has spread peripherally from the breast, the treatment most often recommended is surgery, namely, a mastectomy. Many, if not most, primary operable Stage I and Stage II breast carcinomas can be conservatively managed by partial mastectomy (lumpectomy) plus a standard axillary node dissection, followed by irradiation of the remaining breast tissue. Chemotherapy is sometimes used as an adjuvant to surgery. Radiotherapy may also be used as an adjuvant to surgery, particularly in conjunction with a partial mastectomy and a standard axillary node dissection. For recurrent cancer, palliative radiotherapy can be valuable in controlling local chest wall or cervical lymph node recurrences, and in relieving pain from skeletal metastases.

Hormone therapy, by addition or subtraction, is of greatest use in the palliation of symptoms of breast cancer, or in delaying advance of the disease. Hormone therapy is often combined with radiotherapy when cancer recurs following mastectomy, and when the tumor is so advanced that surgery is contra-indicated or only palliative. The presence or absence of estrogen- and progesterone-receptor protein in primary or metastatic tumor tissue is used to predict which patients may be expected to respond to additive or ablative hormone therapy (Thorpe, 1976).

Cytotoxic chemotherapy is an additional method currently used in the treatment of breast cancer. Prophylactic chemotherapy may be useful in patients at high risk of developing recurrent cancer (i.e., those with axillary lymph node metastases). Chemotherapy is also used in patients with recurrent breast cancer, sometimes in conjunction with hormonal manipulations and/or tamoxifen. The most commonly used, and most effective, chemotherapeutic agent is 5-fluorouracil. Chemotherapeutic agents have demonstrated value in halting or delaying the appearance of metastases, especially in premenopausal patients, and in treating recurrences.

Despite the various mechanisms for detecting, diagnosing, and treating breast cancer, the disease remains the most common cancer in women, and is one of the most fatal (Greenlee et al., 2000). Clearly, alternative strategies for detection of micrometastatic disease, and for more effective and targeted systemic therapies, are needed to improve survival in breast cancer patients. Accordingly, new methods of diagnosis and treatment of breast cancer are still needed, and would be welcome additions to the arsenal of methods currently used in the fight against breast cancer.

SUMMARY OF THE INVENTION

The present invention is based upon the discovery that mammary gland sodium/iodide ($Na^+/I^-$) symporter (mgNIS), a glycoprotein that catalyzes the active transport of iodide, is found in mammary tumoral cells. This discovery has broad implications in the diagnosis and treatment of breast cancer, and in the monitoring of breast cancer therapy.

Accordingly, it is an object of the present invention to provide a method for diagnosing breast cancer in a subject, by detecting expression of mgNIS in breast tissue of the subject.

It is also an object of the present invention to provide a method for treating breast cancer in a subject, by diagnosing breast cancer in the subject by detecting expression of mgNIS in breast tissue of the subject, and treating the breast cancer diagnosed in the subject.

Finally, it is an object of the present invention to provide a method for assessing the efficacy of breast cancer therapy in a subject who has undergone or is undergoing treatment for breast cancer, by monitoring expression of mgNIS in breast tissue of the subject.

Additional objects of the present invention will be apparent from the description which follows.

DETAILED DESCRIPTION OF THE INVENTION

Figure 1:
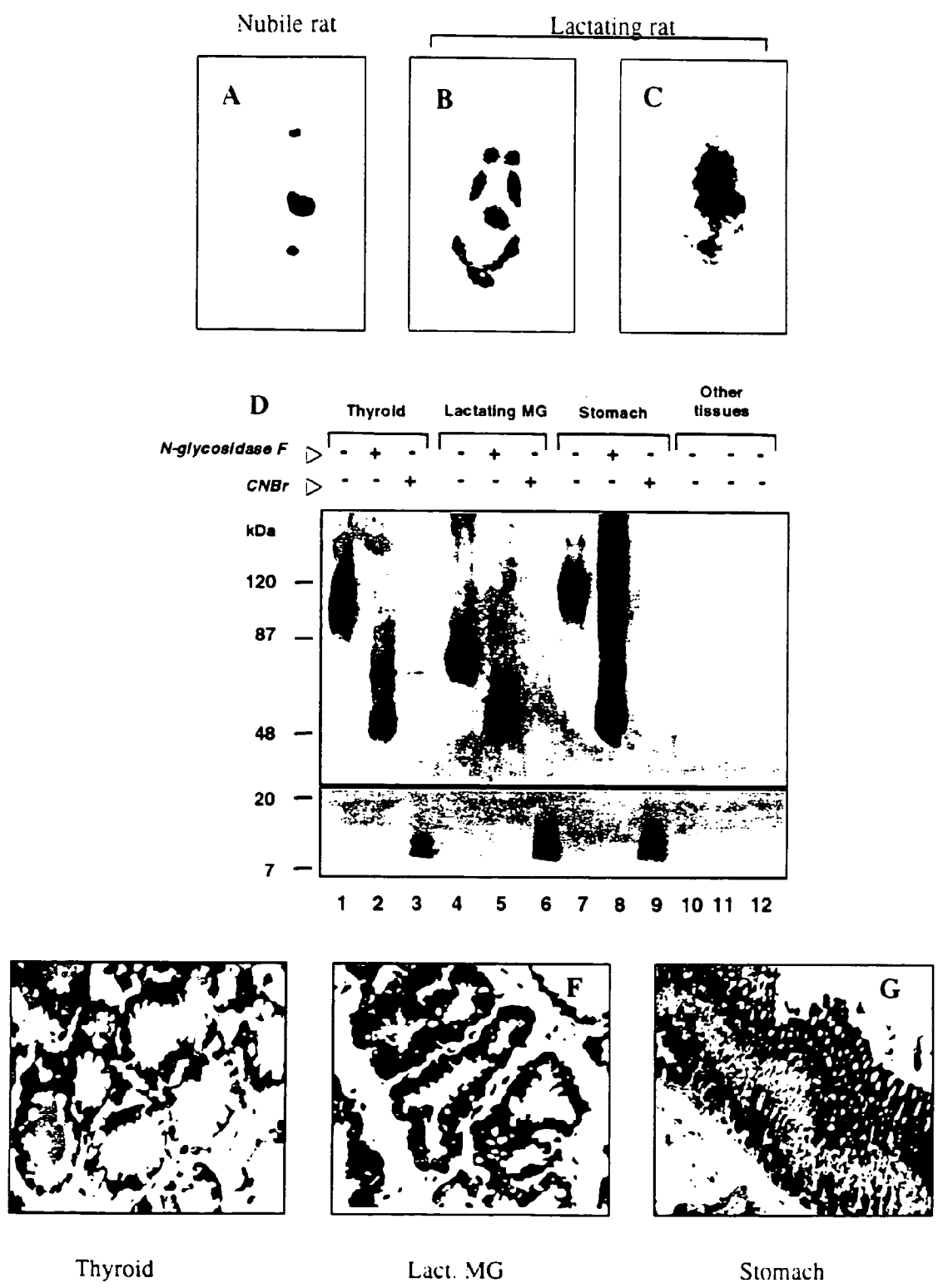
FIG. 1. Characterization of $I^-$ accumulation and NIS expression in rat lactating MG and stomach. (A)-(C) In vivo scintigraphic imaging of $^{99m}TcO_4^-$ injected adult female rats. (A) Radiotracer (1.5 mCi) was injected into the tail vein of nubile animals, and pin-hole images of the body were obtained at 30 min post-injection. (B) Lactating rats were imaged 5 min after $^{99m}TcO_4^-$ injection. (C) To ascertain inhibition of $^{99m}TcO_4^-$ uptake, $^{99m}TcO_4^-$ and 20 mg perchlorate were co-injected into the tail vein, followed by static imaging at 5 min. (D) Immunoblot analysis. Membrane fractions isolated from rat tissues were electrophoresed, electrotransferred onto nitrocellulose, and immunoblotted with affinity-purified anti-NIS antibody (Ab) and horseradish peroxidase (HRP) linked anti-rabbit IgG (Amersham-Pharmacia, Piscataway, N.J.). Approximately 40 µg of membrane fractions were incubated (either with or without N-glycosidase F) overnight at 37° C., followed by SDS polyacrylamide gel electrophoresis and Western blot analysis. Lanes 1 and 2: thyroid; lanes 4 and 5: lactating MG; lanes 7 and 8: stomach; lane 10: non-lactating MG; lane 11: muscle; and lane 12: lung. CNBr-treated membrane fractions from thyroid (lane 3), lactating MG (lane 6), and stomach (lane 9) were electrophoresed, electroblotted onto nitrocellulose, and immunoblotted with anti-NIS Ab, and HRP-linked secondary Ab as described above. Immunohistochemical analysis of rat thyroid (E), lactating MG (F), and stomach (G) tissues was performed with the same anti-NIS Ab. Magnifications: ×200.

The present invention provides a method for diagnosing breast cancer in a subject who has, or may have, breast cancer. As used herein, "subject" is a mammal, including, without limitation, a cow, dog, human, monkey, mouse, pig, or rat, but is preferably a human. The method of the present invention comprises detecting expression of mammary gland sodium/iodide (Na$^+$/I$^-$) symporter (mgNIS) in breast tissue of the subject. As used herein, "mgNIS" includes mgNIS protein, cDNA, and mRNA. The appropriate form of mgNIS will be apparent based on the particular techniques discussed herein. According to the method of the present invention, the expression of mgNIS in breast tissue may be detected in vitro or in vivo. In accordance with the present invention, where expression of mgNIS is detected in vitro, a sample of breast tissue or cells from the subject may be removed using standard procedures, including biopsy and aspiration. Preferably, the sample of breast tissue or cells is removed using multidirectional fine-needle aspiration biopsy (FNAB). This method of removal is preferred, as it is less invasive than a standard biopsy. Cells which are removed from the subject using FNAB may be analyzed using immunocytofluorometry (FACS analysis), for example, as discussed below. Furthermore, the expression of mgNIS in breast tissue may be detected by detection methods readily determined from the known art, including, without limitation, immunological techniques, hybridization analysis, fluorescence imaging techniques, and/or radiation detection.

For example, according to the method of the present invention, the expression of mgNIS may be detected using an agent reactive with mgNIS. As used herein, "reactive" means the agent has affinity for, binds to, or is directed against mgNIS. The agent may be in the form of an antibody, a Fab fragment, an F(ab')$_2$ fragment, a peptide, a polypeptide, a protein, and any combinations thereof. A Fab fragment is a univalent antigen-binding fragment of an antibody, which is produced by papain digestion. An F(ab')$_2$ fragment is a divalent antigen-binding fragment of an antibody, which is produced by pepsin digestion. Preferably, the agent is a high-affinity antibody labeled with a detectable marker. Where the agent is an antibody, the expression of mgNIS may be detected from binding studies using one or more antibodies immunoreactive with mgNIS, along with standard immunological detection techniques, such as Western blotting.

As used herein, the antibody of the present invention may be polyclonal or monoclonal, and may be produced by techniques well known to those skilled in the art. Polyclonal antibody, for example, may be produced by immunizing a mouse, rabbit, or rat with purified mgNIS. Monoclonal antibody may then be produced by removing the spleen from the immunized mouse, and fusing the spleen cells with myeloma cells to form a hybridoma which, when grown in culture, will produce a monoclonal antibody. In addition, the antibodies used herein may be labeled with a detectable marker. Labeling of the antibody may be accomplished using one of the variety of different chemiluminescent and radioactive labels known in the art. The detectable marker of the present invention may be, for example, a nonradioactive or fluorescent marker, such as biotin, fluorescein (FITC), acridine, cholesterol, or carboxy-X-rhodamine, which can be detected using fluorescence and other imaging techniques readily known in the art. Alternatively, the detectable marker may be a radioactive marker, including, for example, a radioisotope. The radioisotope may be any isotope that emits detectable radiation, and need not be a radioactive isotope that is selectively taken up by mgNIS. For example, the radioisotope may include those which are not selectively taken up by mgNIS, such as $^{35}$S, $^{32}$P or $^3$H.

Alternatively, the expression of mgNIS in breast tissue of a subject may be detected through hybridization analysis of nucleic acid extracted from a sample of breast tissue or cells from the subject. According to this method of the present invention, the hybridization analysis may be conducted using one or more nucleic acid probes which hybridize to nucleic acid encoding mgNIS. The probes may be prepared by a variety of techniques known to those skilled in the art, including, without limitation, restriction enzyme digestion of mgNIS nucleic acid; and automated synthesis of oligonucleotides whose sequence corresponds to selected portions of the nucleotide sequence of the mgNIS nucleic acid, using commercially-available oligonucleotide synthesizers, such as the Applied Biosystems Model 392 DNA/RNA synthesizer.

The nucleic acid probes used in the present invention may be DNA or RNA, and may vary in length from about 8 nucleotides to the entire length of the mgNIS nucleic acid. The mgNIS nucleic acid used in the probes may be derived from mammalian mgNIS. The nucleotide sequences for both rat and human NIS are known (Dai et al., 1996a; and Smanik et al., 1996). Using these sequences as probes, the skilled artisan could readily clone corresponding mgNIS cDNA from other species. In addition, the nucleic acid probes of the present invention may be labeled with one or more detectable markers. Labeling of the nucleic acid probes may be accomplished using one of a number of methods known in the art—e.g., nick translation, end labeling, fill-in end labeling, polynucleotide kinase exchange reaction, random priming, or SP6 polymerase (for riboprobe preparation)—along with one of a variety of labels—e.g., radioactive labels, such as $^{35}$S, $^{32}$P, or $^{3}$H, or nonradioactive labels, such as biotin, fluorescein (FITC), acridine, cholesterol, or carboxy-X-rhodamine (ROX). Combinations of two or more nucleic acid probes (or primers), corresponding to different or overlapping regions of the mgNIS nucleic acid, may also be used to detect expression of mgNIS, using, for example, PCR or RT-PCR.

In the further alternative, the expression of mgNIS in breast tissue of a subject may be detected using a detectable agent that is selectively taken up by mgNIS. The detectable agent may be a radioisotope that is selectively taken up by mgNIS. The detectable agent may be, for example, radioiodide ($^{125}$I$^-$ or $^{131}$I$^-$) or $^{99m}$Tc-pertechnetate ($^{99m}$TcO$_4^-$), but is, more preferably, radioiodide. Radioactivity emitted by the radioisotope can be detected by techniques well known in the art. For example, gamma emission from the radioisotope may be detected using gamma imaging techniques, particularly scintigraphic imaging.

The present invention also provides a method for treating breast cancer in a subject or patient. The method of the present invention comprises the steps of: a) diagnosing breast cancer in the subject or patient by detecting expression of mgNIS in breast tissue of the subject or patient; and b) treating the breast cancer diagnosed in the subject or patient. The expression of mgNIS in breast tissue of the subject or patient may be detected by any of the methods described above. The breast cancer diagnosed in the subject or patient may be treated by any method or combination of methods commonly used to treat breast cancer, including, without limitation, surgery, radiotherapy, hormone therapy, chemotherapy, immunotherapy, and systemic therapy. Preferably, however, breast cancer which is diagnosed by detecting expression of mgNIS is treated by an anti-cancer agent that is selectively taken up by mgNIS or an anti-cancer agent that is reactive with mgNIS.

According to the method of the present invention, the breast cancer diagnosed in the subject or patient may be treated by administering to the subject or patient an anti-cancer agent that is selectively taken up by mgNIS. For example, the anti-cancer agent may be a radioisotope which is selectively taken up by mgNIS, and which has an anti-cancer effect. In one embodiment of the present invention, the anti-cancer agent is radioiodide ($^{125}$I$^-$ or $^{131}$I$^-$). Using in vitro assays, it may also be possible to screen for other agents which are selectively taken up by mgNIS. For example, to determine if a particular agent is selectively taken up by mgNIS, the agent may be brought into contact with a sample of tissue or cells known to contain mgNIS, thereby permitting detection of uptake of the agent by mgNIS.

In the alternative, the breast cancer diagnosed in the subject or patient may be treated by administering to the subject or patient an anti-cancer agent that is reactive with mgNIS. Preferably, the anti-cancer agent is a high-affinity antibody bound to a chemotherapeutic cytotoxin. Antibodies directed against mgNIS may be prepared according to the method described above. As used herein, "chemotherapeutic cytotoxin" refers to any chemical substance which kills or destroys malignant breast cells, either independently or in conjunction with an additional agent or treatment. The chemotherapeutic cytotoxin may include any of the anti-cancer drugs or chemotherapeutic agents known in the art, including, for example, chlorambucil, cyclophosphamide, doxorubicin, 5-fluorouracil, melphalan, methotrexate, and vincristine. In addition, the chemotherapeutic cytotoxin may be a photoreactive compound which, when exposed to light of a particular wavelength, undergoes a chemical reaction, and thereby destroys the malignant breast cells.

It is also within the confines of the present invention to use detected levels of mgNIS expression as a clinical or pathologic staging tool, to determine which treatment options may be appropriate. In particular, detected levels of mgNIS expression may be used to determine whether any of the treatment methods of the present invention is appropriate.

The present invention further provides a method for assessing the efficacy of breast cancer therapy in a subject or patient who has undergone or is undergoing treatment for breast cancer. The method of the present invention comprises determining whether mgNIS is expressed in breast tissue of the subject or patient, wherein an absence of mgNIS expression is indicative of successful breast cancer therapy. The expression of mgNIS may be detected by all of the various methods described above. This method of the present invention provides a means of monitoring the effectiveness of breast cancer therapy by permitting the periodic assessment of levels of mgNIS expression in breast tissue of the subject or patient.

According to the method of the present invention, levels of mgNIS expression may be assessed in the subject or patient at any time following the initiation of breast cancer therapy. For example, levels of mgNIS expression may be assessed while the subject or patient is still undergoing treatment for breast cancer. Where levels of mgNIS expression continue to be detected in the breast tissue of the subject or patient, a physician may choose to continue with the breast cancer treatment. Where levels of mgNIS expression decrease through successive assessments, it may be an indication that the breast cancer treatment is working, and that treatment doses could be decreased or even ceased. Where levels of mgNIS do not rapidly decrease through successive assessments, it may be an indication that the breast cancer treatment is not working, and that treatment doses could be increased. Where mgNIS expression is no longer detected in breast tissue of a subject or patient, a physician may conclude that the breast cancer treatment has been successful, and that such treatment may cease. It is also within the confines of the present invention to assess levels of mgNIS expression following completion of the subject's or patient's breast cancer treatment, in order to determine whether breast cancer has recurred in the subject or patient. Furthermore, it is within the confines of the present invention to us assessed levels of mgNIS expression as a clinical or pathologic staging tool, to determine the extent of breast cancer in the subject or patient, to determine appropriate treatment options, and to provide prognostic information.

The present invention is described in the following Experimental Details section, which is set forth to aid in the understanding of the invention, and should not be construed to limit in any way the scope of the invention as defined in the claims which follow thereafter.

Experimental Details

1. Structure and Function of the Sodium/Iodide Symporter

The metabolism of iodide (I$^-$) is commonly associated with the thyroid gland more than with any other tissue or organ in mammals. I$^-$ is an essential constituent of the thyroid hormones $T_3$ and $T_4$. Under physiological conditions, most of the ingested dietary $I^-$ is accumulated in the thyroid by means of a highly specialized active $I^-$ transport mechanism (Carrasco, 1993). $I^-$ transport in the thyroid is catalyzed by the sodium/iodide ($Na^+/I^-$) symporter (NIS), a key glycoprotein located in the basolateral plasma membrane of the thyroid follicular cells (Dai et al., 1996a and 1996b). NIS-catalyzed $I^-$ accumulation is a sodium-dependent active transport process, driven by the $Na^+$ gradient maintained by the $Na^+/K^+$ ATPase. The membrane topology of NIS has been studied by biochemical, biophysical, and immunological techniques. A secondary structure model, predicting 13 transmembrane segments—with an extracellular and an intracellular C-terminus—has been proposed (Levy et al., 1997; and Levy et al., 1998a). Detailed electrophysiological studies have established that NIS activity is electrogenic. Studies have also shown that 2 $Na^+$ ions are transported with one anion, thereby demonstrating unequivocally a 2:1 $Na^+:I^-$ stoichiometry (Eskandari et al., 1997). Several congenital cases of $I^-$ transport defects, arising from mutations in NIS, have been identified (Fujiwara et al., 1997; Matsuda and Kosugi, 1997; and Levy et al., 1998b. For reviews, see De la Vieja et al., 2000; and Dohan et al., 2000). This is a rare condition, most often diagnosed in patients who exhibit co-existence of goiter with congenital hypothyroidism, low or no thyroidal uptake of radioiodide, and little or no $I^-$ uptake by the salivary glands and gastric mucosa.

Other than the thyroid, only a few tissues exhibit active $I^-$ transport. These include lactating mammary gland (MG), salivary glands, and gastric mucosa (Carrasco, 1993). The functional link between $I^-$ transport in the lactating MG and in the thyroid is particularly clear and noteworthy: $I^-$ accumulated in lactating MG, and secreted into milk, is used by the nursing newborn for thyroid hormone biosynthesis (Mountford et al., 1986; and Stubbe et al., 1986). An adequate supply of $I^-$ for sufficient thyroid hormone production is essential for proper development of a newborn's nervous system, skeletal muscle, and lungs (Stubbe et al., 1986; DeGroot, 1989; and Werner and Ingbar, 1991). Severe iodine deficiency at this early stage in life results in mental retardation, and in some cases, dwarfism (Werner and Ingbar, 1991). Like thyroidal $I^-$ transport, $I^-$ is actively translocated in the MG from the bloodstream into the cytoplasm of the epithelial cells, from where it is secreted into the milk.

The degree and pattern of $I^-$ accumulation in the thyroid, as revealed by scintigraphic imaging, is used as an aid in the differential diagnosis of thyroid nodules. Moreover, radioactive $I^-$ (radioiodide) plays a major therapeutic role in the postoperative management of differentiated thyroid carcinoma (DTC) because of its effectiveness in ablating remnant thyroid tissue and metastases (Werner and Ingbar, 1991; Mazzaferri, 1999). In contrast, the ability of mammary tissue to actively transport $I^-$ has not, thus far, been examined for its possible utility in the diagnosis and/or treatment of breast cancer.

2. Materials and Methods

A. Generation of Site-Directed Antibodies

The following peptides, corresponding to C-terminal sequences of human NIS protein, were synthesized by solid phase synthesis (Carrasco et al., 1986) and used to generate polyclonal human anti-NIS antibodies (Abs): peptide P-857, KELEGAGSWTPCVGHD (SEQ ID NO:1), corresponding to residues 618-633, and peptide P-858, GHDGGRDQQETNL (SEQ ID NO:2), corresponding to residues 631-643 of NIS, were used to generate Abs Ct-1 and Ct-2, respectively. The protocol described in Levy et al. (1997) was followed to generate and purify polyclonal antibodies. Peptide NEDLLFFLGQKELE (SEQ ID NO:3), corresponding to residues 598-621, was used to generate the site-directed monoclonal Ab, as described in Harlow and Lane (1988).

B. Immunohistochemical Analysis

Immunoreactivity was carried out using the immunoperoxidase method (Amenta and Martinez-Hernandez, 1995). In brief, 5 μm sections were deparaffinated through 3 changes of xylene, followed by passage through alcohols to distilled water. All slides were subjected to antigen retrieval using 10% citrate buffer (DAKO Carpinteria, Calif.). Thereafter, slides were cooled and rinsed twice in TBST solution (0.3 M of NaCl, 0.1% Tween 20, and 0.05 M of Tris-HCl) (pH:7.6) for 5 min. All incubations were carried out in a humid chamber at room temperature, and all subsequent washes were done with TBST. Endogenous biotin activity was blocked with sequential avidin biotin incubation (DAKO Biotin Blocking System, Carpenteria, Calif.), followed by serum-free protein block provided in the Catalyzed Signal Amplification kit (DAKO, Carpinteria, Calif.), as indicated by the supplier. Slides were incubated for 15 min with anti-rat NIS, Ct-1, Ct-2, or monoclonal primary Abs diluted in the provided blocking solution to a concentration of 1:500 (rat tissues), 1:600 (human breast, polyclonal Abs), 1:750 (human thyroid, polyclonal Abs), and 1:100 (human tissues, monoclonal Ab), respectively. The initial concentration of polyclonal and monoclonal Abs were 1 μg/μl and 0.5 μg/μl, respectively. Tissues were sequentially incubated with biotinylated secondary antibodies, then streptavidin, followed by an amplification step performed with biotinyl tyramide, as described by the supplier (DAKO, Carpinteria, Calif.). Lastly, slides were incubated with streptavidin-horseradish peroxidase prior to chromogen reaction using diaminobenzidine (DAB) tetrachloride Tris-HCl buffer (pH 7.6) containing 0.8% peroxide, for 3 to 5 min. Sections were rinsed in water, dehydrated in graded ethanols, counterstained or mounted with permount, and examined by light microscopy. Immunoreactivity was competitively inhibited in the presence of 0.7 μM of corresponding synthetic peptides used to generate Abs. Non-specific immunoreactivity was evaluated with unrelated rabbit and mouse immunoglobulins (DAKO Carpenteria, Calif.). CAM 5.2 Ab against low molecular weight keratins 8 and 18 (Becton Dickinson, San Jose, Calif.) was used to identify epithelial cells. All counterstains for immunohistochemical studies were done with Toluidine blue. Immunoreactivity was analyzed by light microscopy and graded on a scale of 0 to 4+. Tissues were judged positive for NIS expression when at least 20% or more of the cells exhibited ≧2+.

C. Hormonal Treatment of Animals

Oxytocin (α-hypophamine), prolactin, progesterone (4-pregnene-3,20-dione), and 17-β-estradiol (1,3,5[10]-estratriene-3,17-β-diol) were purchased from Sigma, St. Louis, Mo. Either ovariectomized or surgically unmodified 8- to 10-week-old CD1 (ICR) IBR mice (Charles River Laboratories, Wilmington, Mass.) were treated once a day with subcutaneous injections of 1 I.U. of oxytocin, 10 I.U. of prolactin, 1 μg 17-β-estradiol, or 1 I.U. of progesterone (intraperitoneally) for three consecutive days, either individually or in the indicated combination. A final injection was done on the fourth day; two hours later, mammary glands were removed for analysis. Oxytocin and prolactin were dissolved in sterile distilled water, 17-β-estradiol was dissolved in 90% alcohol, and progesterone was dissolved in sesame oil (Sigma, St. Louis, Mo.). Except for progesterone, indicated doses of hormones were injected after being taken in 200 µl sterile PBS solution. Progesterone (final concentration 10 mg/ml) was injected into 100 µl of sesame oil. Control animals which were sham treated with sesame oil were systematically included in experiments when progesterone was administered. At least three identically-treated animals were analyzed in each case.

D. In Vivo Transport Studies

1 µCi of $^{125}I^-$ (100 mCi/ml, Amersham-Pharmacia, Piscataway, N.J.) was added to 100 µl of PBS and intraperitoneally administered to hormonally-treated animals. One hour later, animals were sacrificed, and various organs were surgically removed and placed in pre-weighted eppendorf tubes. Approximately 500 µl of blood was also taken from the inferior vena cava of each animal during surgery. Tubes were weighed and counted in a γ-counter (LKB-Wallac, Gaithersburg, Md.). Radioactivity accumulated in each organ was determined in terms of cpm/mg of tissue, standardized with radioactivity detected per mg of blood, and expressed as the ratio of cpm detected in the organ of interest versus blood. Data were obtained from the analysis of at least three animals in each experiment.

E. Tissue Retrieval and Immunoblot Analysis

Sprague-Dawley female rats (over 8 weeks old) at different physiological stages, and hormonally-treated CD1 (ICR) BR female mice, were sacrificed in a $CO_2$ chamber before excision of thoracic, abdominal, and inguinal MG. Organs, which were removed from mice or rats were blended with a polytron homogenizer (Brinkmann Instruments, Westbury, N.Y.) for 1 min, and homogenized with a stirrer-type glass-teflon homogenizer (Caframo-Wiarton, Ontario, Canada) (Levy et al., 1997). Membrane fractions were prepared in the presence of protease inhibitors, as described above (Kaminsky et al., 1994). SDS-PAGE electrophoresis and electroblotting to nitrocellulose were performed as described in Levy et al. (1997). All samples were diluted 1:2 with loading buffer (Harlow and Lane, 1988) and heated at 37° C. for 30 min prior to electrophoresis. Immunoblot analyses were carried out with 2 µg of affinity-purified anti-NIS Ab (Levy et al., 1997) and a 1:1500 dilution of a horseradish peroxidase-linked donkey anti-rabbit IgG (Amersham-Pharmacia, Piscataway, N.J.). Both incubations were performed for 1 h. Polypeptides were visualized by the enhanced chemiluminescence (ECL) Western blot detection system (Amersham-Pharmacia, Piscataway, N.J.).

F. Peptidyl N-Glycosidase F Treatment

Membranes (40 µg) were resuspended in 10 µl of 0.5 M Tris-HCl (pH 8.0), and 18 µl of water was added with either 3 µl of N-glycosidase F (600 milliunits, Boehringer Mannheim) or 2 µl of 50% glycerol. Membranes were then incubated overnight at 37° C. (18 h). After overnight incubation, samples were diluted 1:2 with loading buffer (15 µl) and incubated at 37° C. for 30 min prior to electrophoresis (Levy et al., 1997).

G. CNBr Fragmentation of Proteins

Pieces of nitrocellulose containing the corresponding immunoreactive NIS species were excised and cut into smaller pieces of ~1 mm×2 mm, then incubated for 1 h in the dark, at room temperature, with 300 µl of CNBr (~300 mg/ml) in 70% formic acid. Samples were centrifuged to pellet the nitrocellulose pieces; the formic acid containing the released digested peptides was lyophilized in a speed-vac at medium heat (~1 h). Dried peptides were resuspended in 75 µl water and lyophilized again, followed by resuspension into sample buffer (30 µl). Samples were neutralized with a small volume (<5 µl) of 100 mM of Tris (pH 9.1) prior to 15% SDS/PAGE electrophoresis.

H. Cell Aspiration and FACS Analysis

A multidirectional fine-needle aspiration biopsy (FNAB) from the tumor was performed with a 22-gauge needle connected to a 20 ml plastic syringe that was attached to a metal holder. The aspirate was resuspended and fixed in CytoLyt solution (Cyto Corporation, Boxborough, Mass.), maintained at 4° C., and analyzed within 24-48 hr. The cells which were resuspended in the CytoLyt solution were then passed through a 35-mm nylon mesh, centrifuged at 500 g, and resuspended and permeabilized in PBS (phosphate buffered saline) containing 0.1% BSA (bovine serum albumin) and 0.2% saponin (PBSAP). 200,000 cells/tube were incubated for 1 hr at room temperature in 100 ml PBSAP containing 10-80 nM of one of the two affinity-purified antiNIS antibodies raised against the intracellular C-terminal end of NIS (antiKELE *..antiETNL).

After washing in 1 ml PBSAP, the cells were incubated for 1 hr on ice, in the dark, with fluorescein isothiocyanate (FITC)-conjugated antirabbit IgG antibody in 100 µl of BSA-SAP-PBS (1:1000 dilution). Cells were washed once again with 1 ml of BSA-SAP-PBS, and resuspended in 300 µl of PBS. The fluorescence of 10,000 cells per tube was assayed by flow immunocytofluorometry (FACScan; Becton Dickinson & Co., Mountainview, Calif.); threshold and forward scatter was used to gate the cells and eliminate debris and cell aggregates. A histogram plot was generated, and mean fluorescence intensity of each sample was determined using CELLQuest software.

2. Results

A. Physiology and Regulation of $I^-$ Transport in Mammary Tissue

I. In Vivo Analysis of $I^-$ Accumulation in Rat Mammary Tissue

To characterize the active accumulation of $I^-$ in milk, lactating rats were administered a single $^{125}I^-$ intraperitoneal injection, and the time course of $^{125}I^-$ transport was assessed in milk samples at given intervals. $^{125}I^-$ was concentrated more than ~60 fold in milk with respect to blood, with saturation occurring at ~2 h (not shown). $^{125}I^-$ was also concentrated in lactating MG; however, it was not concentrated in skeletal muscle from the same rat, or in MG from a non-lactating female rat. To assess the overall tissue distribution of $I^-$ in vivo, $^{131}I^-$ or pertechnetate ($^{99m}TcO_4^-$) was administered to female rats that were then imaged by scintigraphy. $^{99m}TcO_4^-$, a gamma emitter that is actively concentrated in the thyroid by thyroid NIS (tNIS), offers the practical advantage of a much shorter half-life ($t_{1/2}$=6 h) than $^{131}I^-$ ($t_{1/2}$=8 days) (Papadopoulos et al., 1967). Therefore, $^{99m}TcO_4^-$ was used in most experiments.

When injected into non-lactating rats, the radioisotope was initially (30 min) observed primarily in the stomach, whereas at later time points it was concentrated predominantly in the thyroid (FIG. 1A). In stark contrast, in lactating rats, $^{99m}TcO_4^-$ was visualized in the stomach and was then rapidly concentrated (within 5 min) in all pairs of MGs (FIG. 1B), thereby demonstrating an avid concentrating activity of the anion in lactating MG. In lactating animals, $^{99m}TcO_4^-$ eventually accumulates in the thyroid as well (not shown). Simultaneous injection of perchlorate—a potent inhibitor of active $I^-$ transport (Carrasco, 1993)—and $^{99m}TcO_4^-$ into a lactating rat effectively prevented $^{99m}TcO_4^-$ concentration in thyroid, stomach, and lactating MG (FIG. 1C). The pattern shown in FIG. 1C corresponds to distribution of $^{99m}TcO_4^-$ in the vascular compartment and the urinary tract, without active accumulation of $^{99m}TcO_4^-$ in any tissue, as a result of the blocking effect of perchlorate. These data show that $^{131}I^-/^{99m}TcO_4^-$ accumulation in the thyroid, lactating MG, and stomach, as observed by scintigraphic imaging, is specific and inhibited by perchlorate.

II. Identification of Mammary Gland NIS (mgNIS)

The availability of anti-NIS antibody (Ab) raised against rat tNIS made it possible for the first time to apply an immunological approach to attempt the specific identification of mgNIS (Levy et al., 1997). Anti-NIS Ab reacts with a rat tNIS polypeptide of ~100 kDa (Levy et al., 1997) (FIG. 1D, lane 1). The same Ab identified a single broad polypeptide of ~75 kDa in rat lactating MG membranes, i.e., mgNIS (FIG. 1D, lane 4). In contrast, immunoreactivity was absent in non-lactating MG (FIG. 1D, lane 10) and in membranes from lung and muscle—tissues that do not actively transport I$^-$ (FIG. 1D, lanes 11 and 12). Immunoreactivity against both the ~75 and ~100 kDa polypeptides was competitively blocked by addition of the synthetic eliciting peptide that contains the last 16 amino acids of NIS (not shown).

Given that tNIS is known to be a highly glycosylated protein (Levy et al., 1997 and 1998a), the difference in electrophoretic mobilities between tNIS (~100 kDa) and mgNIS (~75 kDa) may represent differences in glycosylation. To investigate this possibility, alkaline-extracted membrane proteins from thyroid and lactating MG were treated with N-glycosidase F, an enzyme that removes N-linked carbohydrates. Under these conditions, anti-NIS Ab recognized a ~50 kDa polypeptide in either thyroid (FIG. 1D, lane 2) or lactating MG (FIG. 1D, lane 5). Significantly, both non-glycosylated NIS in FRTL-5 cells (a line of highly functional thyroid cells) and NIS expressed in E. coli exhibited an identical electrophoretic mobility (i.e., ~50 kDa) (Levy et al., 1997). Therefore, the ~75 kDa and ~50 kDa immunoreactive polypeptides detected in lactating MG are glycosylated and non-glycosylated mgNIS, respectively. These findings are consistent with the recently reported full identity between cDNAs that encode the human thyroid and mammary NIS proteins (Spitzweg et al., 1998).

Immunoreactivity against a gastric polypeptide of ~110 kDa was also observed with anti-NIS Ab (FIG. 1D, lane 7), and was blocked by excess synthetic NIS carboxy terminus peptide (not shown), consistent with the accumulation of I$^-$ in stomach (FIG. 1A). Upon deglycosylation the gastric polypeptide also migrated at ~50 kDa (FIG. 1D, lane 8), strongly suggesting that these polypeptides correspond, respectively, to the glycosylated and non-glycosylated species of the gastric I$^-$ transporter (gNIS). Methionine-specific cleavage of tNIS, mgNIS, and gNIS using CNBr indicates that NIS is the same protein in each of the three tissues—thyroid, mammary gland, and gastric (FIG. 1D, lanes 3, 6, and 9).

In addition, immunohistochemical analysis was carried out on formalin-fixed paraffin-embedded tissue sections derived from rat thyroid, MG, and stomach. Distinct basolateral plasma membrane reactivity was evident in the thyroid follicular cells (FIG. 1E), lactating MG epithelial cells (FIG. 1F), and the surface epithelial cells of the gastric mucosa (FIG. 1G). Notably, basal chief cells exhibited less NIS immunoreactivity, whereas parietal cells were entirely devoid of immunoreactivity. As in the immunoblots, immunoreactivity was absent in striated muscle, cartilage, and nubile MG (not shown). Taken together, all the above observations indicate that active I$^-$ accumulation in the thyroid, lactating MG, and stomach is mediated by NIS.

III. Expression of mgNIS in Various Physiological Stages

The expression of mgNIS was analyzed in nubile, lactating, and previously lactating (PL) MG (i.e., MG of dams separated from their litters). Considerable morphological changes are evident in the MG during gestation and lactation. The fatty stroma, characteristic of the nubile gland (FIG. 2A), is replaced by alveolar-ductal structures containing luminal secretions and epithelial cells with intracellular milk fat globules (Joshie et al., 1976; and Dulbecco et al., 1982) (FIG. 2B). Weaning promotes rapid involutional changes, such as alveolar dilatation and flattening of the epithelium (Helminen et al., 1968; and Martinez-Hernandez et al., 1976) (FIG. 2C). Alkaline-extracted membranes from MG tissue in each of the above-mentioned stages were subjected to immunoblot analysis. mgNIS was absent in nubile MG (FIG. 2D, lane 1), but clearly present in lactating MG (FIG. 2D, lane 2). Twenty-four hours after weaning, mgNIS expression was significantly decreased in PL MG (FIG. 2D, lane 3), and by 48 h mgNIS was not detectable (FIG. 2D, lane 4). Remarkably, mgNIS expression was reversible upon re-initiation of suckling (FIG. 2D, lane 5). Clearly, mgNIS expression is upregulated during lactation, rapidly down-regulated upon cessation of lactation, and exquisitely regulated in a reversible manner by suckling.

To investigate whether mgNIS expression starts in response to suckling or before (i.e., during gestation), immunoblot analysis was conducted on membrane fractions from MGs during various stages of the mice 20-day gestation period (FIG. 2E). Expression of a ~75 kDa mgNIS protein was barely detectable at mid-gestation (lane 11d), whereas higher levels of mgNIS expression, together with a significant increase in $^{125}I^-$ transport in MG cells, were reached towards the end of gestation (FIGS. 2E and 2F, lane 18d). These data clearly indicate that the induction of mgNIS expression precedes suckling (FIG. 2E); however, after delivery, suckling is essential for continued milk production and increased expression of mgNIS in the mammary epithelial cells (FIG. 2D).

B. Hormonal Regulation of mgNIS Expression

I. Effects of Oxytocin and Prolactin on mgNIS Expression in Intact Animals

Figure 3:
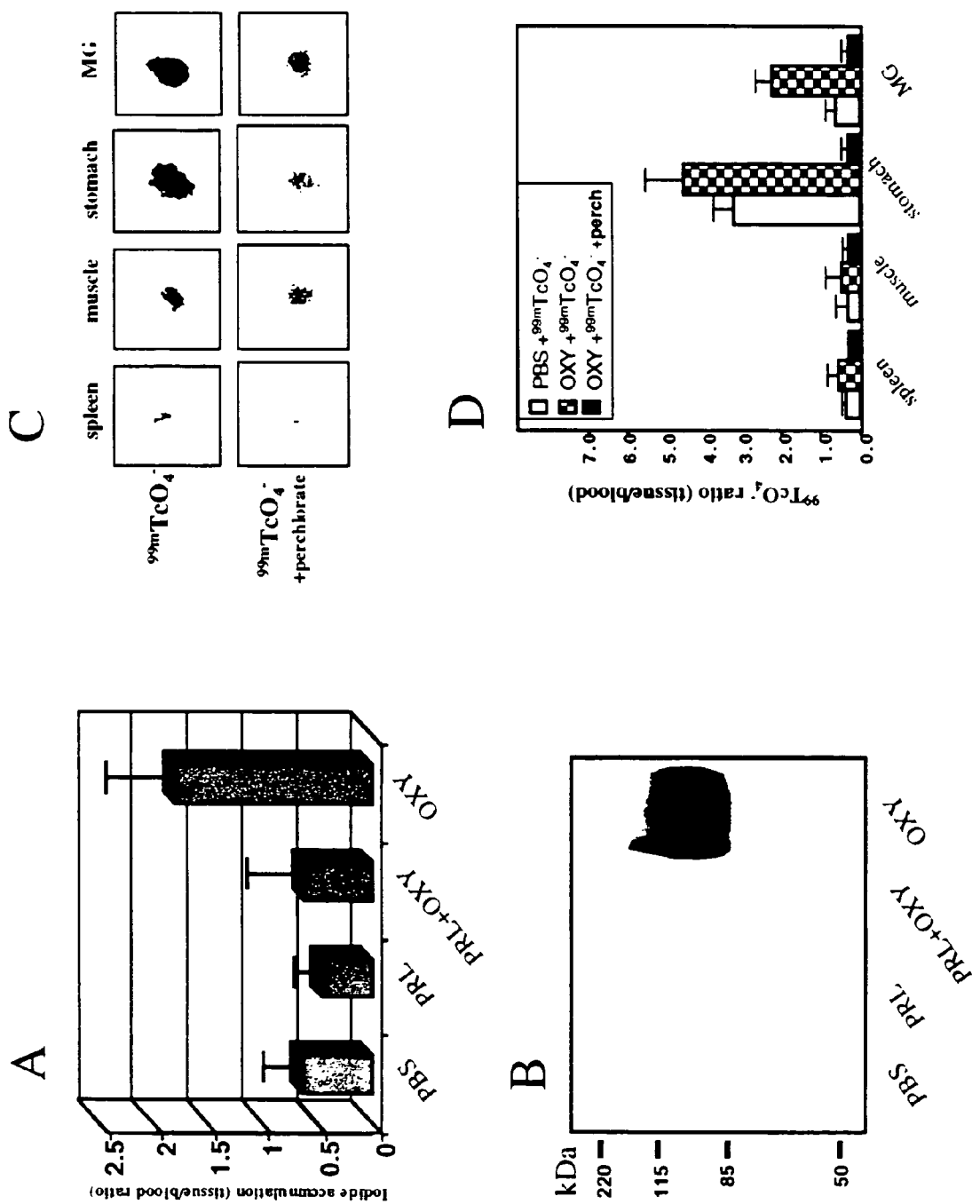
FIG. 3. In vivo effect of oxytocin on functional expression of mgNIS in nubile mice. (A) Radioiodide transport in MG of oxytocin-treated nubile mice. Seven- to eight-week-old female mice were treated subcutaneously with phosphate buffered saline solution (PBS), 10 I.U. of prolactin (PRL), 1 I.U. of oxytocin (OXY), or prolactin and oxytocin (PRL+OXY) for three days. Then, 1 µCi of $^{125}I^-$ was injected intraperitoneally. One hour later, MG were surgically removed and tracer accumulation was quantified in a γ-counter (LKB 1282 Compugamma, Md.). Obtained values were standardized according to the weight of removed tissue, and expressed as the ratio of radioiodide in MG tissue versus blood. (B) Immunoblot analysis of MG from hormonally-treated mice. Membrane fractions isolated from MG of nubile female mice were either sham treated with PBS, or hormonally-treated (as described in (A)) with prolactin (PRL), prolactin and oxytocin (PRL+OXY), or oxytocin (OXY), as described in (A). Isolated membrane fractions were electrophoresed, electrotransferred onto nitrocellulose, and analyzed by immunoblots using anti-NIS Ab. (C) Ex vivo scintigraphic imaging of $^{99m}TcO_4^-$ distribution in tissues from oxytocin-treated nubile mice. Oxytocin-treated animals (n=4) were divided into two groups. One group was intravenously injected with $^{99m}TcO_4^-$ through the tail, while the other group received $^{99m}TcO_4^-$ together with 2 mg of perchlorate. Thirty minutes later, spleen, and skeletal muscle from the limb, stomach, and MG, were removed from both groups of animals (upper squares: $^{99m}TcO_4^-$; lower squares: $^{99m}TcO_4^-$+perchlorate), and placed 4 cm apart from each other on a petri dish. Images of organs were then obtained with a pin-hole gamma camera for 5 min. Perchlorate-inhibited accumulation of $^{99m}TcO_4^-$ was detected in stomach and MG of OXY-treated animals. (D) Quantification of $^{99m}TcO_4^-$ accumulation in various organs from OXY- or PBS-treated mice. Tracer accumulation was monitored using image analysis software (ImageQuant, Macintosh). Regions of interest were drawn around removed individual organs, and average counts per pixel were obtained. Counts were divided by the weight of the organs (cpm/mg tissue), and standardized by dividing them by cpm detected in the blood (cpm/mg blood) of each animal. $^{99m}TcO_4^-$ accumulation in the organs from: PBS-treated animals (open bars); OXY-treated animals (dotted bars); and OXY-treated animals after $^{99m}TcO_4^-$+perchlorate injection (dark bars).

In all mammals, mammary gland development, milk protein synthesis, and lactation result from the combined effects of, among others, estrogen, progesterone, prolactin, and oxytocin (Lyons et al., 1958; and Topper et al., 1981). In mice, prolactin, a glycoprotein released from the anterior pituitary, plays an essential role in lobuloalveolar development of the mammary gland during gestation, and in the induction of synthesis and secretion of milk proteins (Vonderhaar, 1987). For its part, oxytocin, a nonapeptide hormone released from the posterior pituitary, is essential for the milk ejection response to suckling during lactation (Young et al., 1996). Intact and ovariectomized (see following section) adult nubile mice were systematically treated with various combinations of these hormones, then analyzed for mgNIS expression using immunohistochemistry and immunoblot analysis. As both prolactin and oxytocin are released simultaneously in response to suckling (Wakerley et al., 1978; and Higushi et al., 1985), nubile rats and mice were treated with these hormones to discern whether the reversible suckling-dependent upregulation of mgNIS expression is caused by oxytocin, prolactin, or both. It was observed that oxytocin alone (but not in combination with prolactin) induced mgNIS expression (FIG. 3B, lane OXY), leading to $^{125}I^-$ transport in MG tissue (FIG. 3A). This demonstrates that the functional expression of mgNIS is upregulated by oxytocin, even in nubile animals, and that this regulatory effect is unexpectedly antagonized by prolactin. The ability of oxytocin to induce mgNIS expression in the relatively undeveloped and undifferentiated MG of nubile animals indicates that mgNIS synthesis can occur independently of gestation and lactation-related changes. The antagonist effect of prolactin on oxytocin action was an unexpected result because mgNIS is upregulated in response to suckling, which, as indicated above, stimulates the release of both hormones (Wakerley et al., 1978; and Higushi et al., 1985). This observation is further analyzed below.

Significant increases in mgNIS activity, due to oxytocin administration, were also demonstrated in mice by scintigraphic imaging (FIGS. 3C and 3D). In nubile mice, surgical removal of the MG for imaging purposes was necessary to differentiate between the signals from the stomach and those from the few epithelial cells present in the MG. Oxytocin-treated and sham-treated nubile mice received a single dose of $^{99m}TcO_4^-$, with or without perchlorate. Thirty minutes later, internal organs were surgically removed and $^{99m}TcO_4^-$ accumulation in individual organs was monitored with a pin-hole gamma-camera (FIG. 3C). The accumulation of tracer in these organs was quantified (FIG. 3D). As expected, accumulation of $^{99m}TcO_4^-$ in the stomach of both oxytocin-treated and sham-treated animals was significantly higher than in the spleen or skeletal muscle from the limb (FIGS. 3C and 3D). This accumulation of $^{99m}TcO_4^-$ was inhibited by perchlorate, revealing that the tracer was transported specifically via mgNIS. Thereafter, accumulation of tracer in MGs from oxytocin-treated animals was compared with accumulation in MGs from sham-treated animals. Perchlorate-inhibited $^{99m}TcO_4^-$ accumulation in MGs was significantly higher in oxytocin-treated than in sham-treated mice (FIG. 3D). The levels of mgNIS expression in imaged MGs of oxytocin-treated animals were similar in all individual mice tested, as assessed by immunoblot analysis (not shown). Thus, the $^{99m}TcO_4^-$ accumulation in MGs of these animals is due to perchlorate-inhibited mgNIS activity, and not to individual variations in mgNIS expression. In conclusion, results from transport assays (FIGS. 3A and 3D), immunoblot analysis (FIG. 3B), and scintigraphic imaging (FIG. 3C) demonstrate that functional mgNIS expression is upregulated by an increase in the circulating concentration of oxytocin in nubile animals.

Figure 4:
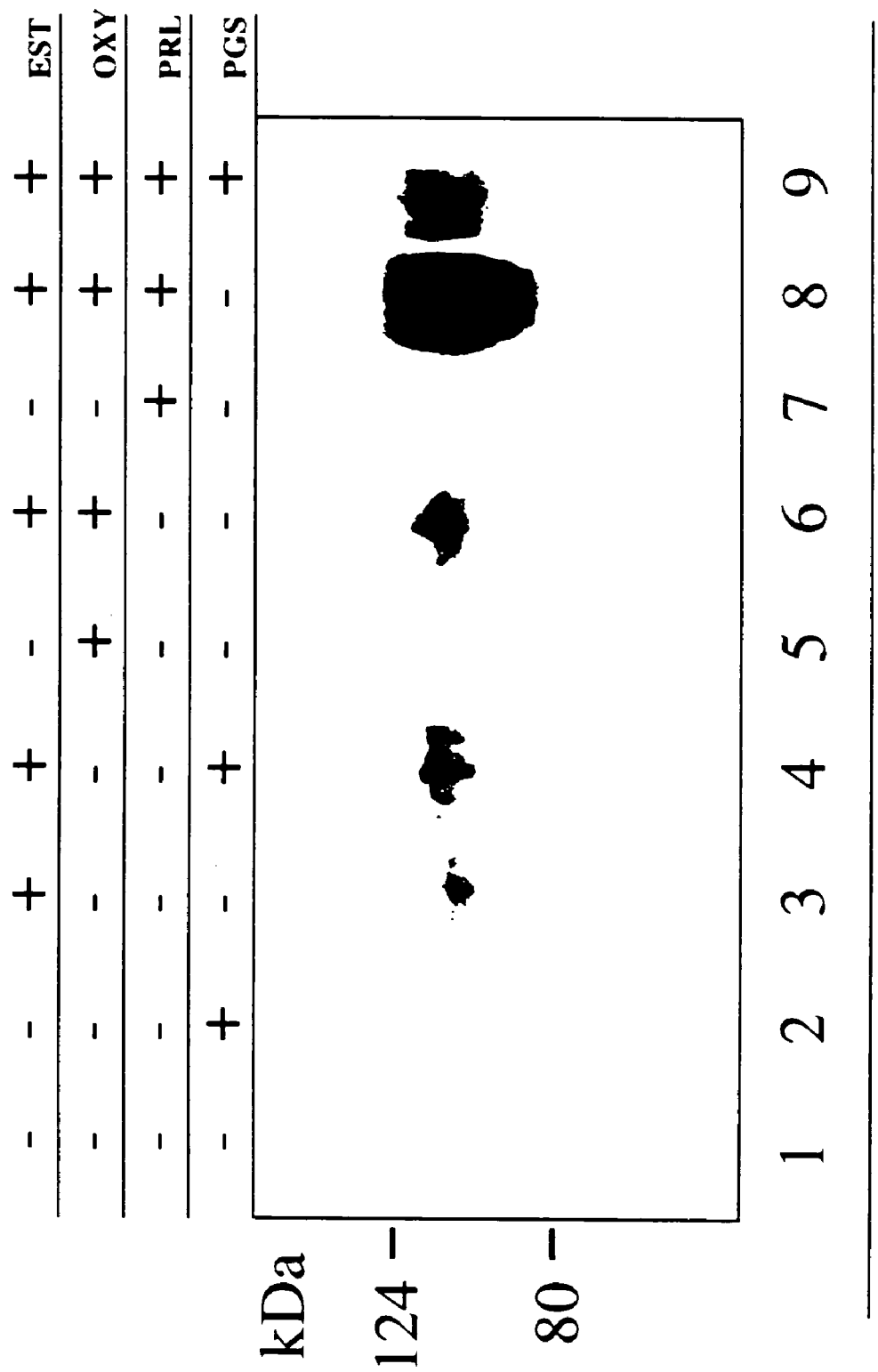
FIG. 4. Immunoblot analysis of MG from ovariectomized nubile mice treated with various hormones. Membrane fractions isolated from MG of nubile mice were either sham treated with PBS (lane 1) or treated for three consecutive days with: progesterone (1 I.U.) (lane 2); 17-β-estradiol (1 µg) (lane 3); 17-β-estradiol and progesterone (1 I.U.) (lane 4); oxytocin (1 I.U.) (lane 5); oxytocin and 17-β-estradiol (lane 6); prolactin (10 I.U.) (lane 7); oxytocin, prolactin, and 17-β-estradiol (lane 8); and progesterone together with oxytocin, prolactin, and 17-β-estradiol (lane 9). Isolated membrane fractions were electrophoresed and electrotransferred onto nitrocellulose, followed by immunoblot analysis with anti-NIS Ab.

II. Effects of 17-β-Estradiol, Progesterone, Oxytocin, and Prolactin in Ovariectomized Mice To further examine the hormonal regulation of mgNIS expression, and particularly to assess the roles of gonadal steroid hormones (estrogens and progesterone), nubile ovariectomized (OVX) adult mice were used. Mice were administered 17-β-estradiol, progesterone, oxytocin, and prolactin, both individually and in different combinations, and mgNIS expression was assessed in mammary tissue by immunoblot analysis (FIG. 4). No mgNIS expression was detected in control PBS-treated animals (FIG. 4, lane 1). Significantly, administration of oxytocin alone to ovariectomized mice did not cause an increase in mgNIS expression (FIG. 4, lane 5), starkly contrasting with the effect of oxytocin in intact animals (FIG. 3B). Indeed, of all the hormones tested individually, only 17-β-estradiol led to a clearly discernible increase in mgNIS expression (FIG. 4, lane 3). Combined administration of 17-β-estradiol and oxytocin resulted in mgNIS expression (FIG. 4, lane 6) modestly higher than 17-β-estradiol alone (FIG. 4, lane 3), suggesting that the upregulating effect of oxytocin on mgNIS expression may require estrogen. Although it has not been studied in mammary tissue, estrogen has been reported to upregulate accumulation of the oxytocin receptor gene mRNA in the uterine epithelium and hypothalamus of the rat (Larcher et al., 1994; and Bale and Dorsa, 1995 and 1997). A similar effect of estrogen in the breast would be consistent with the inventors' observations.

By far the greatest increase in mgNIS expression was observed upon administration of 17-β-estradiol, oxytocin, and prolactin together (FIG. 4, lane 8). This indicated that, not only does prolactin not antagonize the upregulating effect of oxytocin, it actually enhances it when estrogen levels are high. The antagonizing action of prolactin on oxytocin upregulation of mgNIS expression in intact nubile mice clearly occurs in the presence of comparatively lower (endogenous) estrogen levels (see above section). Tellingly, when progesterone was added to the 17-β-estradiol/oxytocin/prolactin combination, mgNIS expression was significantly decreased (FIG. 4, lane 9). Contrastingly, a comparison of mgNIS expression in estrogen-treated versus estrogen- and progesterone-treated animals revealed that progesterone did not interfere with 17-β-estradiol enhancement of mgNIS expression (FIG. 4, lanes 3 and 4). These observations are consistent with the notion that progesterone may act as an oxytocin inhibitor due to competitive binding of progesterone to the oxytocin receptor in the breast, much as it reportedly occurs in the uterus (Fuchs et al., 1983; and Grazzini et al., 1998). In conclusion, the combination of estrogen, prolactin, and oxytocin (in the absence of progesterone) leads to the highest mgNIS expression in ovariectomized mice. This combination of hormones closely resembles the relative hormonal levels prevalent in mice and rats during lactation (McCormack and Greenwald, 1974; and Rosenblatt et al., 1988), when the action of mgNIS as an I⁻ supplier to the nursing pups is most beneficial.

C. Active I⁻ Transport in Experimental Mammary Tumors

I. Expression and Activity of mgNIS in Experimental Mammary Tumors in Transgenic Mice In the course of breast development, the menstrual cycle, gestation, and lactation, mammary epithelial cells undergo extensive proliferation, differentiation, and involution in response to hormonal regulation. Physiologically, MG epithelial cells express mgNIS only during lactation, following the culmination of intense glandular proliferation and differentiation. Because neoplastic transformation represents an abnormal proliferative process with altered cellular differentiation (Fitzgibbons et al., 1998), it seems plausible that mgNIS could be expressed in cancer. The inventors sought to assess whether mgNIS is functionally expressed in experimental mammary tumors in female transgenic mice carrying either an activated ras (a cytoplasmic GTPase) oncogene or overexpressing the neu oncogene, each of them under the transcriptional control of the MMTV promoter/enhancer (Sinn et al., 1987; and Guy et al., 1992). The tyrosine kinase receptor encoded by the neu (known as c-erbB2 in humans) proto-oncogene is amplified and overexpressed in as many as 30% of human breast cancers (Slamon et al., 1987; Paterson et al., 1991; DiGiovanna, 1999; and Siegel et al., 1999).

Figure 5:
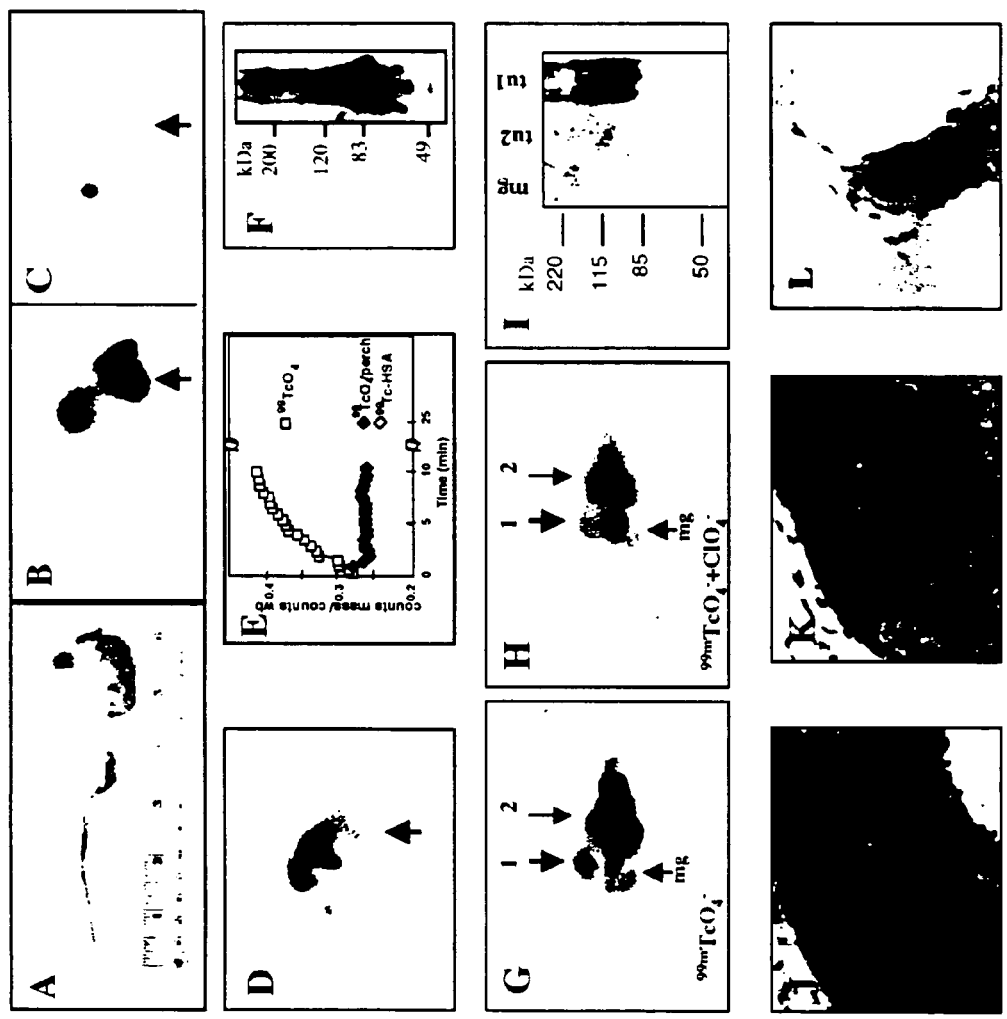
FIG. 5. Analysis of mammary adenocarcinomas in MMTV-ras and MMTV-neu transgenic mice. (A) Photograph of MMTV-ras transgenic mouse with a mammary adenocarcinoma. Transgenic mice were anaesthetized with intramuscular sodium pentobarbital injections. Then, $^{99m}TcO_4^-$ (B, G), $^{99m}Tc$-labeled human serum albumin ($^{99m}Tc$-HSA) (C), or $^{99m}TcO_4^-$+perchlorate (D, H) was administered by tail vein injections. (E) Dynamic curves of percent injected dose per pixel were calculated by drawing regions of interest around tumoral tissue and the mediastinum, and dividing the counts per pixel (average counts) within each region of interest by the initial whole-body count value, thereby yielding a percent injected dose per pixel. (F) Immunoblot analysis of membrane fractions isolated from MMTV-ras tumor with anti-NIS Ab. (I) Immunoblot analysis of membrane fractions isolated from MMTV-neu tumors with anti-NIS Ab. In an MMTV-neu mouse with two adjacent mammary glands containing tumors, each tumor is indicated with an arrow and numbered. Lanes "tu1", "tu2", and "mg" correspond to proteins extracted from tumor 1, tumor 2, and contralateral normal mammary gland, respectively. (J) Tissue section exhibiting intense immunoreactivity to anti-NIS Ab in this poorly-differentiated adenocarcinoma, and (K) parallel section in the same area of "tu1" reacting with anti-HER-2/neu Ab. (L) Contralateral normal gland ("mg") exhibiting ductal structure surrounded by fatty stroma, demonstrating no reactivity to HER-2/neu. Magnifications: ×200.

To assess whether specific active I⁻ uptake (a result of mgNIS expression) occurred in the mammary tumoral cells, transgenic animals were imaged in vivo with either $^{131}$I⁻ or $^{99m}TcO_4^-$. The results were striking. Specific active $^{99m}TcO_4^-$ transport in the tumors was indeed demonstrated on imaging. First, injected $^{99m}TcO_4^-$ was accumulated in the stomach and tumor (FIG. 5B for an MMTV-ras mouse and 5G for an MMTV-neu mouse). Second, $^{99m}TcO_4^-$ accumulation was prevented when the isotope was co-injected with perchlorate (FIG. 5C for MMTV-ras and 5H for MMTV-neu), thereby showing that the observed accumulation in the tumor and stomach was specifically mediated by NIS. Injection of $^{99m}$Tc-HSA, a vascular space marker that is distributed non-specifically solely according to blood pool, showed that the observed accumulation pattern in the MMTV-ras tumor was not due to non-specific increase of the blood pool (FIG. 5D). Quantification of the accumulation of the various tracers in the tumor, as a function of time, is also shown for the ras mouse. The quantification values underscore both the absence of tumoral accumulation of $^{99m}TcO_4^-$ when co-injected with perchlorate, and the lack of accumulation of the vascular space marker (FIG. 5E).

MMTV-ras and MMTV-neu mice were subsequently sacrificed, and tumoral tissue was retrieved for histological, immunohistochemical, and immunoblot analysis. Both kinds of transgenic animals developed mammary adenocarcinomas that were high-grade, poorly differentiated, estrogen- and progesterone-receptor negative (not shown), and positive for mgNIS expression by immunohistochemistry. The mgNIS immunohistochemical staining pattern of the tumors was intracellular, and not merely evident exclusively at the plasma membrane (FIG. 5J). Furthermore, mgNIS expression was demonstrated by immunoblot analysis in both ras (FIG. 5F) and neu (tu1) (FIG. 5I) tumors, showing that I⁻ transport activity is concomitant with mgNIS protein expression. Immunoblot analysis of non-tumoral MG tissue from the contralateral side of the same MMTV-neu mouse revealed no mgNIS expression (FIG. 5I). Parallel tissue sections probed with anti-HER-2/neu Ab demonstrated that neu expression was absent from normal glands, but was significant in transformed MG, especially in the mgNIS-expressing tumor (FIGS. 5K and 5L). This indicates that any factors that led to the expression and activation of mgNIS in tumoral mammary tissue were not operative in non-tumoral tissue in the same neu mouse. No $^{99m}TcO_4^-$ transport activity was observed using imaging, and no mgNIS expression was detected using immunoblots, either in a second carcinoma in the same MMTV-neu mouse (tu2) (FIG. 5I) or in the tumor of a different MMTV-neu mouse (not shown). These observations indicate that the absence of tracer uptake in these tumors, based on imaging, correlates with lack of mgNIS expression in the same tumors, based on immunological analysis. In conclusion, functional expression of mgNIS has been demonstrated in experimental mammary tumors caused in transgenic mice by activation or overexpression of the ras and neu oncogenes. Because increased amplification of the neu gene homologue in humans (c-erbB2) correlates with highly aggressive tumors with negative prognosis even for patients without lymph node involvement (Guy et al., 1992; and Siegel et al., 1999), these findings in experimental mouse models may be relevant to human breast cancer. The results suggest that mgNIS might be expressed in human breast tumors, that these tumors might be clinically detected by scintigraphic imaging, and that mgNIS-mediated transport might provide an alternative modality for the detection and/or treatment of breast tumors and metastatic disease.

D. Expression of mgNIS in Human Breast Cancer

Figure 6:
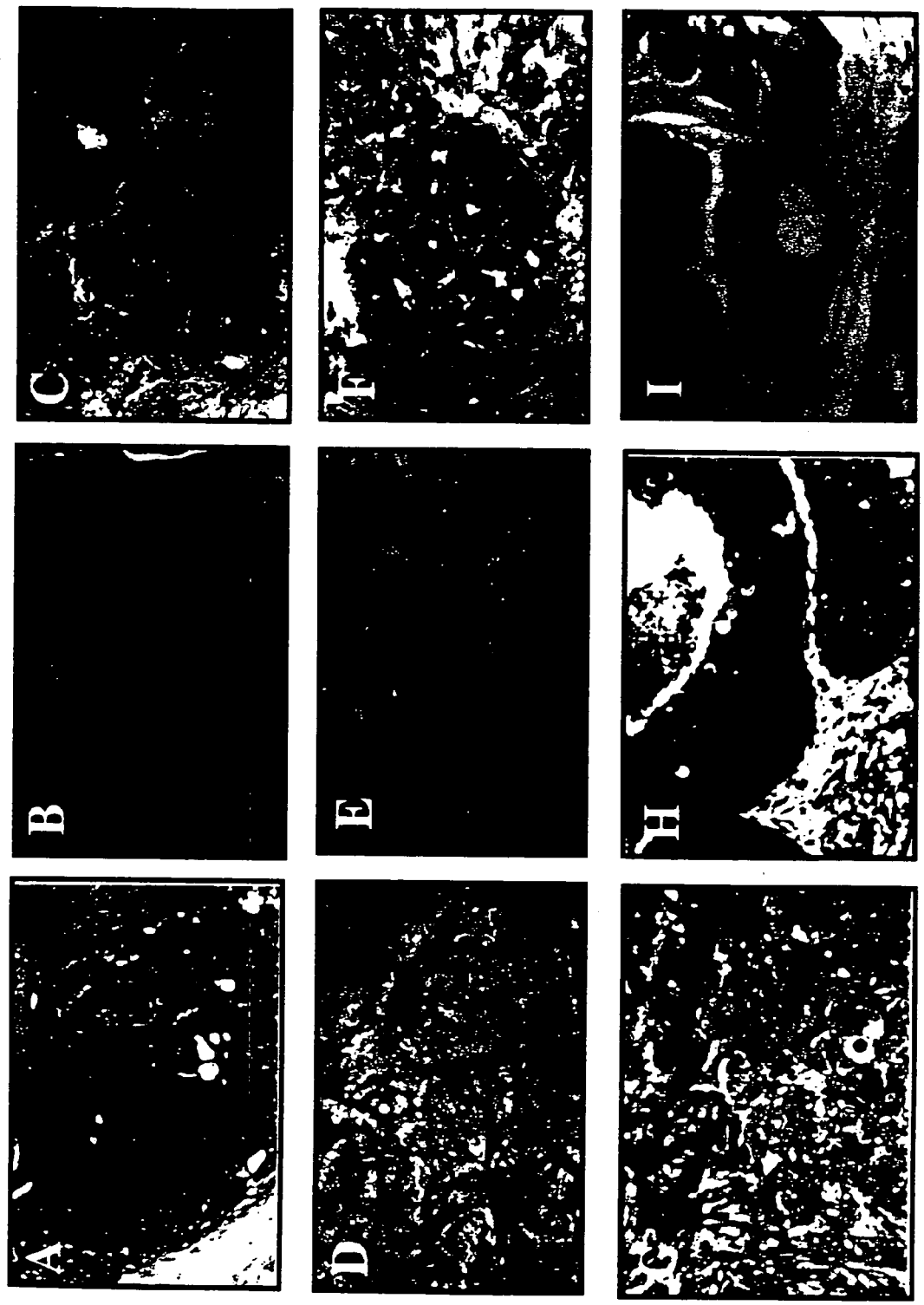
FIG. 6. Immunohistochemical expression of NIS in human thyroid and breast tissues. (A) Papillary carcinoma of the thyroid, revealing distinct malignant cell NIS immunoreactivity with polyclonal anti-NIS Ct-2 Ab. Magnification: ×12. (B) Parallel section demonstrating competitive inhibition of mgNIS expression in the presence of Ct-2 peptide. Magnification: ×12. (C) Invasive ductal carcinoma of the breast. mgNIS expression is detected with polyclonal anti-NIS Ct-2 Ab. Magnification: ×16. (D) Competitive inhibition of immunoreactivity with corresponding peptide. Magnification: ×16. (E) Parallel section treated with monoclonal anti-NIS Ab, again showing identical distribution of immunoreactivity as shown in (C). Magnification: ×16. (F) Normal ductal-lobular units in the vicinity of the breast cancer shown in (C) and (E), as detected with monoclonal anti-NIS Ab. Magnification: ×40. (G) Higher magnification of another invasive ductal carcinoma, showing focal areas of immunoreactivity with a very distinct intracellular staining pattern. Magnification: ×160. (H) Ductal carcinoma in situ featuring intraductal comedonecrosis and intense immunoreactivity (>95%) of malignant cells, as detected with monoclonal anti-NIS Ab. Magnification: ×66. (I) Gestational breast tissue manifesting characteristic adenomatous-lactational changes which occur in the latter half of pregnancy, and demonstrating mgNIS expression in epithelial cells, as probed with polyclonal anti-NIS Ct-2 Ab. Magnification: ×80.

Having shown that mgNIS is functionally expressed in experimental transgenic mice adenocarcinomas, the inventors examined human breast tissue specimens (29 malignant [23 invasive carcinomas and 6 ductal carcinomas in situ], 13 non-tumoral from tissue in the vicinity of the tumors, and three biopsies from pregnant women) for mgNIS expression (Table 1). Specimens were studied by immunohistochemical analysis using two site-directed polyclonal (Ct-1 and Ct-2) anti-NIS Abs and one monoclonal anti-NIS Ab, each of the three directed against different epitopes of the C-terminus of human NIS (FIG. 6) (see Materials and Methods). In all experiments, competitive inhibition of immunoreactivity with the C-terminal eliciting peptide verified the specificity of the antibody reaction (FIG. 6D). As an additional control, the use of rabbit and mouse immunoglobulins against unrelated antigens confirmed that no staining resulted from non-specific immunoreactivity with human antigens other than mgNIS in breast tissue. Breast epithelial cells were identified on parallel sections with anti-cytokeratin Abs (Zeng et al., 1999) to distinguish them from other stromal cell populations (not shown). Sections were graded by the intensity of the immunoperoxidase reaction on a scale of 0 to 4+, and by the percentage of reacting epithelial cells. Tissues exhibiting 2+ to 4+ staining in 20% or more of the epithelial cells were considered positive for mgNIS expression. Archival thyroid specimens displaying clear mgNIS expression, both in differentiated thyroid cancerous areas (either papillary or follicular) and in adjacent normal-appearing follicles, were selected as positive experimental controls (FIG. 6A, thyroid papillary carcinoma; FIG. 6B, competitive inhibition of immunoreactivity with C-terminal eliciting peptide).

The findings (summarized in Table 1) were compelling: 87% of the 23 invasive breast cancers (FIGS. 6C, E, and G) and 83% of the 6 ductal carcinomas in situ (FIG. 6H) expressed mgNIS, as compared to only 23% of the 13 non-cancerous samples adjacent to, or in the vicinity of, the tumors (FIG. 6F). Ductal carcinomas in situ (FIG. 6H), in which mgNIS expression was as marked as in invasive carcinomas (FIGS. 6C, E, and G), are associated with an increased risk of developing a subsequent invasive carcinoma (Fitzgibbons et al., 1998), and represent a possible intermediate step between benign atypical ductal hyperplasia and invasive carcinoma (Rosen, 1997). The pattern of mgNIS expression in all malignant breast cells (FIGS. 6C, E, G, and H) was identical to that noted in control thyroid sections (FIG. 6A), consisting of a predominant granular pattern of intracellular distribution that suggests organellar localization of NIS. This contrasts with the distinct basolateral plasma membrane staining observed in rat mammary gland tissues (FIG. 1F).

TABLE 1 mgNIS expression in human breast cancer

| Breast Histology | Number | mgNIS Positive | Estrogen Receptor Positive |
| --- | --- | --- | --- |
| Invasive carcinomas | 23 | 20 (87%) | 56% |
| Ductal carcinoma in situ | 6 | 5 (83%) | ND* |
| Noncancerous in vicinity of tumor | 13 | 3 (23%) | ND* |
| Gestational tissues | 3 | 3 (100%) | ND* |

ND*: not determined

Staining in non-cancerous samples that were mgNIS-positive (FIG. 6F) was less intense than in malignant tissue (FIGS. 6C, E, G, and H). All three gestational biopsies exhibited florid adenomatous-lactational changes characteristic of this physiological stage, and were clearly mgNIS positive (FIG. 6I). In two of these gestational samples, the epithelial cells within the fibroadenomatous tissue displayed florid hyperplasia, similar to the non-affected adjacent tissue (not shown). This suggests that mgNIS expression in fibroadenomatous tissue is responsive to hormonal changes that take place during gestation. Interestingly, mgNIS expression was noted throughout the gestational tissue sampled, including areas with distinct basolateral plasma membrane immunoreactivity (FIG. 6I) similar to lactating rat mammary gland (FIG. 1F). The observed expression of mgNIS in gestational samples is consistent with the upregulation of mgNIS during pregnancy and lactation (see previous sections).

In conclusion, over 80% of the breast cancers analyzed express mgNIS, suggesting that mgNIS is frequently upregulated during malignant transformation in human breast. The high prevalence of mgNIS expression in human breast cancer, and the observation in transgenic mice that mgNIS-positive tumors exhibit active $I^-$ transport, together suggest that radioiodide is potentially a novel alternative therapeutic modality in breast cancer.

3. Discussion

A. mgNIS Catalyzes Active $I^-$ Transport in Rat Lactating Mammary Glands

The ability of cancerous thyroid cells to actively accumulate $I^-$ via thyroid NIS (tNIS) provides a unique and effective delivery system to detect and target these cells for destruction with therapeutic radioiodide, largely without harming other tissues. The effectiveness of radioiodide therapy in treating thyroid cancer relies on the capacity of malignant thyroid cells to retain sufficient $I^-$ transport activity to accumulate the isotope, even though this activity is decreased, relative to healthy thyroid cells, as a result of malignant transformation. In fact, a major characteristic of the healthy thyroid gland is that it exhibits tNIS activity for life, within boundaries set by such thyroid regulatory factors as TSH and $I^-$ itself (Levy et al., 1997; and Eng et al., 1999). In contrast, the potential effectiveness of radioiodide therapy in breast cancer depends on whether mgNIS becomes functionally expressed in cancerous mammary cells as a result of malignant transformation, given that mgNIS is normally not expressed in healthy epithelial mammary cells, except during pregnancy and lactation. Thus, it is notable that a single transport protein—NIS—catalyzes the same fundamental process—active $Na^+$-dependent $I^-$ transport—in both of these tissues, but is regulated differently in each. These differences affect not only how NIS functions in health, but also how it can play a role in cancer management in both tissues. Insofar as NIS is functionally expressed to a sufficient degree in cancerous cells, whether of thyroid, breast, or any other origin, radioiodide emerges as a proven and effective therapeutic tool.

As shown in FIG. 1, $I^-$ transport in rat lactating mammary glands is pronounced, active, specific, and inhibited by perchlorate, as assessed in vivo both by tracking the accumulation of $I^-$ in milk and by analyzing the tissue distribution of $I^-$ by scintigraphy. This indicates that $I^-$ transport in rat lactating mammary glands is a protein-mediated active transport process. mgNIS has been identified as a single broad polypeptide of ~75 kDa in rat lactating mammary gland membranes, as observed by immunoblot analysis with anti-NIS Abs raised against tNIS. It has also been demonstrated that mgNIS is identical to both tNIS and gNIS, although it is differently glycosylated than either of them in their respective tissues. Consistent with this, the presence of identical NIS transcripts has been reported in rat thyroid, mammary gland, and stomach (Spitzweg et al., 1998). Thus, it is clearly established that mgNIS is the protein that catalyzes active $I^-$ transport in rat lactating mammary glands.

Figure 2:
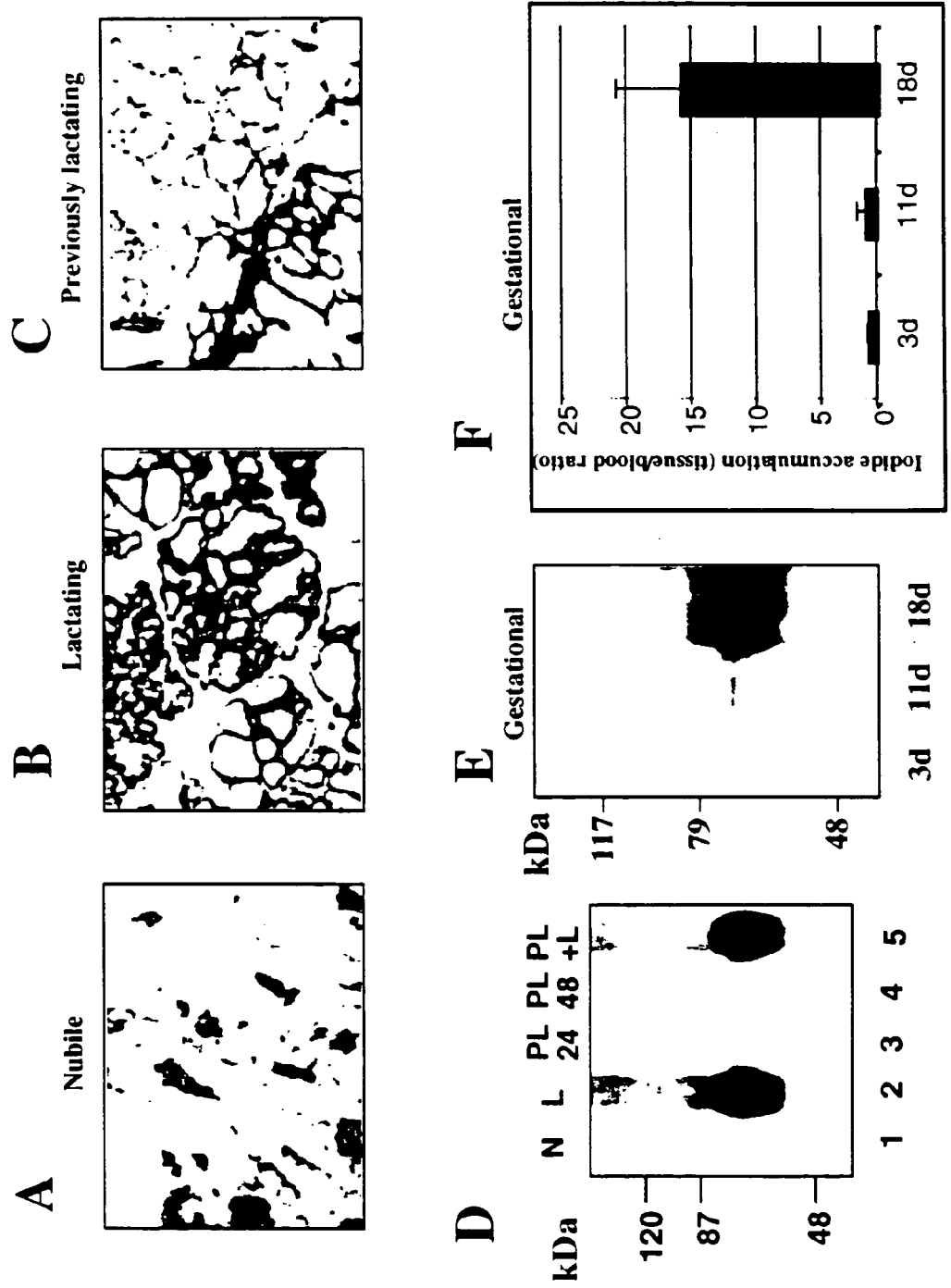
FIG. 2. Analysis of mgNIS expression in murine MG at different physiological stages. Fresh-fixed, snap-frozen tissue sections of nubile (A), lactating (B), and previously lactating (48 h after weaning of pups) (C) MGs, with hematoxylin and eosin staining. Magnifications: ×30. (D) Immunoblot analysis with anti-NIS Ab. MG membrane fractions (40 µg) from nubile animals (lane 1); lactating dams (lane 2); and lactating dams after litter weaned for 24 h (lane 3), for 48 h (lane 4), and for 48 h followed by re-establishment of nursing for 24 h (lane 5). (E) Immunoblot analysis of MG at various stages of gestation with anti-NIS Ab. Membrane fractions (40 µg) of MG tissue, prepared from mice at the third (3d), eleventh (11d), and eighteenth (18d) days of gestation, were analyzed by immunoblots using anti-NIS Ab, as described above. (F) Radioiodide accumulation in MG from mice at various stages of gestation. Animals at indicated days of gestation ($3^{rd}$, $11^{th}$, or $18^{th}$) received a single dose of 1 µCi $^{125}I^-$ by subcutaneous injection in 100 µl of PBS. One hour later, MG were surgically removed, and radioactivity was quantified in a γ-counter (LKB 1282 Compugamma, Md.). Obtained values were standardized according to the weight of MG removed from each mouse, and were expressed as the ratio of radioiodide in MG tissue versus blood.

B. Oxytocin, Prolactin, Estradiol, and Progesterone Play Significant Roles in the Regulation of mgNIS Expression To initiate the identification of factors involved in the regulation of mgNIS, mgNIS expression was examined in nubile, pregnant, lactating, and previously lactating rats and/or mice by immunohistochemistry and immunoblot analysis, as well as by in vivo scintigraphic imaging (FIGS. 1 and 2). Findings indicated that mgNIS is barely detectable at any time other than lactation and the second half of gestation. At approximately mid-gestation, mgNIS becomes detectable; thereafter, its expression increases considerably as gestation progresses (FIG. 2E). By the 18th day of gestation in mice, the MG show a 15-fold accumulation of subcutaneously-injected radioiodide, as compared with the blood concentration of the tracer. Therefore, suckling is not required for the functional expression of mgNIS. Still, both suckling and its cessation clearly become the major stimuli that regulate the functional expression of mgNIS after delivery (FIG. 2D). These findings suggest that there are suckling-dependent and suckling-independent factors that regulate the functional expression of mgNIS.

The inventors first considered the effect of suckling-dependent hormones, oxytocin and prolactin, on mgNIS expression. The striking ability of oxytocin alone to induce functional mgNIS expression in nubile animals has already been mentioned above (FIG. 3), as has the surprising antagonistic effect of prolactin on mgNIS upregulation by oxytocin. Interestingly, the relative migration of oxytocin-induced mgNIS from nubile animals is slightly slower (100 kDa) (FIG. 3B, lane 4) than mgNIS from lactating animals (~75 kDa) (FIG. 2D, lane 2). This difference is due to glycosylation, as the relative migration of mgNIS from either group of animals (oxytocin-treated nubile as compared to lactating) becomes indistinguishable upon deglycosylation (not shown). It is significant that the first enzyme in the N-linked glycosylation pathway, UDP-GlcNAc:dolichol phosphate N-acetylglucosamine-1-phosphate transferase (GPT), is constitutively expressed in all tissues except mammary gland, where its expression is modulated by lactogenic hormones (Rajput et al., 1994; and Ma et al., 1996). This suggests that differences in the levels of lactogenic hormones between oxytocin-treated nubile and intact lactating animals are likely to account for the observed glycosylation differences in mgNIS.

Subsequent studies of suckling-independent hormonal regulators of mgNIS expression, such as estradiol and progesterone, also shed light on the effects of the suckling-dependent hormones, oxytocin and prolactin (FIG. 4). The inventors' findings may be summarized as follows: 1. in ovariectomized mice, 17-β-estradiol alone caused a pronounced increase of mgNIS; 2. in contrast to its effect in intact animals, oxytocin alone did not increase mgNIS expression in ovariectomized animals; 3. in ovariectomized animals, combined 17-β-estradiol and oxytocin led to a modestly higher expression of NIS than did 17-β-estradiol alone; 4. maximum mgNIS expression resulted from a combination of 17-β-estradiol, oxytocin, and prolactin in ovariectomized animals, even though prolactin antagonized mgNIS upregulation by oxytocin in intact animals; 5. progesterone inhibits the stimulatory effect on mgNIS expression of combined 17-β-estradiol, oxytocin, and prolactin.

The above results indicate that a threshold level of circulating estrogens is necessary for optimal mgNIS expression overall, and, in particular, for the upregulation of mgNIS by oxytocin. The co-operative role played by estrogens in regard to oxytocin's effect on mgNIS may be explained by the likelihood that the oxytocin receptor gene mRNA is upregulated by estrogen in the breast, as it has been reported in the hypothalamus and uterus (Zingg et al., 1995 and 1998). In addition, a direct effect of estrogen on mgNIS transcription could also occur. Consistent with this notion is the observation that the NIS promoter contains several half-site estrogen responsive elements (EREs) (Ohno et al., 1999). Hence, oxytocin alone increases mgNIS expression in intact animals, in which endogenous estrogens are present, but not in ovariectomized animals, in which estrogens are absent.

In intact animals, prolactin's antagonistic effect on the increase of mgNIS expression by oxytocin may be due to the reported inhibitory effect of prolactin on steroidogenesis (Dorrington and Gore-Langdon, 1981 and 1982; Gitay-Goren et al., 1989; Krasnow et al., 1990; and Villanueva et al., 1996). In intact (non-gestational, non-lactating) animals, exogenous prolactin would cause endogenous estrogen levels, which are lower than in gestational or lactating animals, to decrease below the threshold, thereby preventing concomitantly-administered oxytocin from stimulating mgNIS expression. On the other hand, no antagonistic effect of prolactin administered simultaneously with oxytocin is observed in ovariectomized animals that received a high amount of exogenous estrogen. Under these conditions, steroidogenesis is entirely bypassed. Moreover, the results show that prolactin actually leads to higher mgNIS expression when given, together with estrogen and oxytocin, to ovariectomized animals (FIG. 4, lane 8). This suggests that, in the presence of high levels of estrogen, prolactin may have a separate direct or indirect stimulatory effect on mgNIS expression by a mechanism currently unknown. It appears that endogenous oxytocin increases mgNIS expression in lactating animals, despite the presence of endogenous prolactin, because, under the hormonal conditions of lactation, steroidogenesis most probably overcomes the steroidogenesis-inhibitory effect of prolactin. The concentration of endogenous prolactin in intact animals, even during lactation, is considerably lower (~1.2 µg/ml) than the one used experimentally (300 µg/injection) (Mattheij et al., 1982). Hence, during lactation, estrogens would remain above the necessary threshold necessary for oxytocin to stimulate mgNIS expression, and for prolactin to enhance, rather than antagonize, this effect.

Finally, given the central role played by oxytocin in the increase of mgNIS expression, it is likely that the ability of progesterone to inhibit the stimulatory effect on mgNIS expression of combined 17-β-estradiol, oxytocin, and prolactin may involve a direct inhibition of oxytocin-receptor signaling by competitive binding of progesterone to the oxytocin receptor in the breast. This non-genomic effect of progesterone has, thus far, been observed in the uterus (Fuchs et al., 1983; Grazzini et al., 1998; and Zingg et al., 1998). In addition, it is possible that progesterone also inhibits oxytocin receptor gene expression in the breast, as proposed for the regulation of this gene in the cervix of the uterus (Umscheid et al., 1998). The fall of progesterone levels in mammals following delivery, therefore, coexists with the onset of suckling and the release of oxytocin. According to the inventors' results, this would, in turn, optimize the ability of oxytocin to upregulate mgNIS expression during lactation.

C. mgNIS is Functionally Expressed in Experimental Mammary Tumors in Transgenic Mice, and is Detectable by Scintigraphic Imaging In Vivo The studies of experimental mammary tumors in transgenic mice, as described above, seemed potentially relevant to human breast cancer because the inventors were addressing a fundamental biological question conceivably applicable to all mammals: Can malignant transformation of mammary epithelial cells lead to functional expression of mgNIS? The results (FIG. 5) provide compelling evidence that the answer to this question is yes: scintigraphic imaging in vivo dramatically demonstrated pronounced, active, specific, and perchlorate-inhibited mgNIS activity in mammary tumors of non-gestational and non-lactating female transgenic mice which either carried an activated ras oncogene or overexpressed the neu oncogene. Immunoblot analysis (using anti-NIS Ab) of mammary tissue from these mice demonstrated a correlation between mgNIS activity observed by scintigraphy and mgNIS expression: mgNIS was expressed only in tumoral mammary tissues that had displayed mgNIS activity. No mgNIS expression was detected in non-tumoral mammary tissue (which, without exceptions, exhibited no mgNIS activity), or even in non-I⁻-transporting tumoral mammary tissue. Thus, malignant mammary cells are detectable by in vivo scintigraphic imaging in mice, and could, therefore, be specifically targeted for destruction with higher doses of radioiodide.

D. mgNIS is Specifically Expressed in >80% of Human Breast Cancer Tumors, as Detected by Immunohistochemistry with Anti-NIS Abs It remained to be revolved whether mgNIS is expressed in human breast tumors, and, if so, whether the prevalence of mgNIS expression in breast cancer is high. The finding that >80% of the analyzed human breast cancer samples expressed mgNIS in at least 20% of their cells (Table 1 and FIG. 6) resolves both of these issues in the affirmative. In all cases, mgNIS expression detected by immunohistochemistry was specific, as it was inhibited by excess C-terminus eliciting peptide. However, a wide variety of immunohistochemical pattern was observed from one tumor to another. Some tumors exhibited diffuse, moderate to light immunoreactivity in nearly all of their cells (FIGS. 6C and 6E); others showed distinct areas of complete negativity interspersed with focal areas of intense positivity, or a single confined positive region (FIG. 6G). In stark contrast, only 23% of non-cancerous tissue samples that were either adjacent to or in the vicinity of the tumors showed mgNIS staining; moreover, even when present, staining was noticeably less pronounced (FIG. 6F) than in tumoral samples (FIGS. 6C, 6E, and 6H). Therefore, as in transgenic mice, mgNIS is expressed in humans primarily in neoplastic mammary tissue, as a result of malignant transformation; it is not expressed to any significant extent in apparently healthy tissue.

The expression of mgNIS during gestation appears to be an indicator of the physiological, hormone-driven differentiation of breast epithelial cells from non-lactating to lactating. Nevertheless, the degree to which some mgNIS expression was observed in non-cancerous (and non-lactating) tissue samples in the vicinity of the tumors may reflect either the presence of morphologically normal cells in the early stages of malignant transformation, or low-grade mgNIS expression in actually healthy cells. In any case, the above results suggest that therapeutic doses of radioiodide could be used in humans to selectively destroy breast cancer cells, provided mgNIS is functional in human breast cancer, as it is in transgenic mice mammary tumors.

Figure 7:
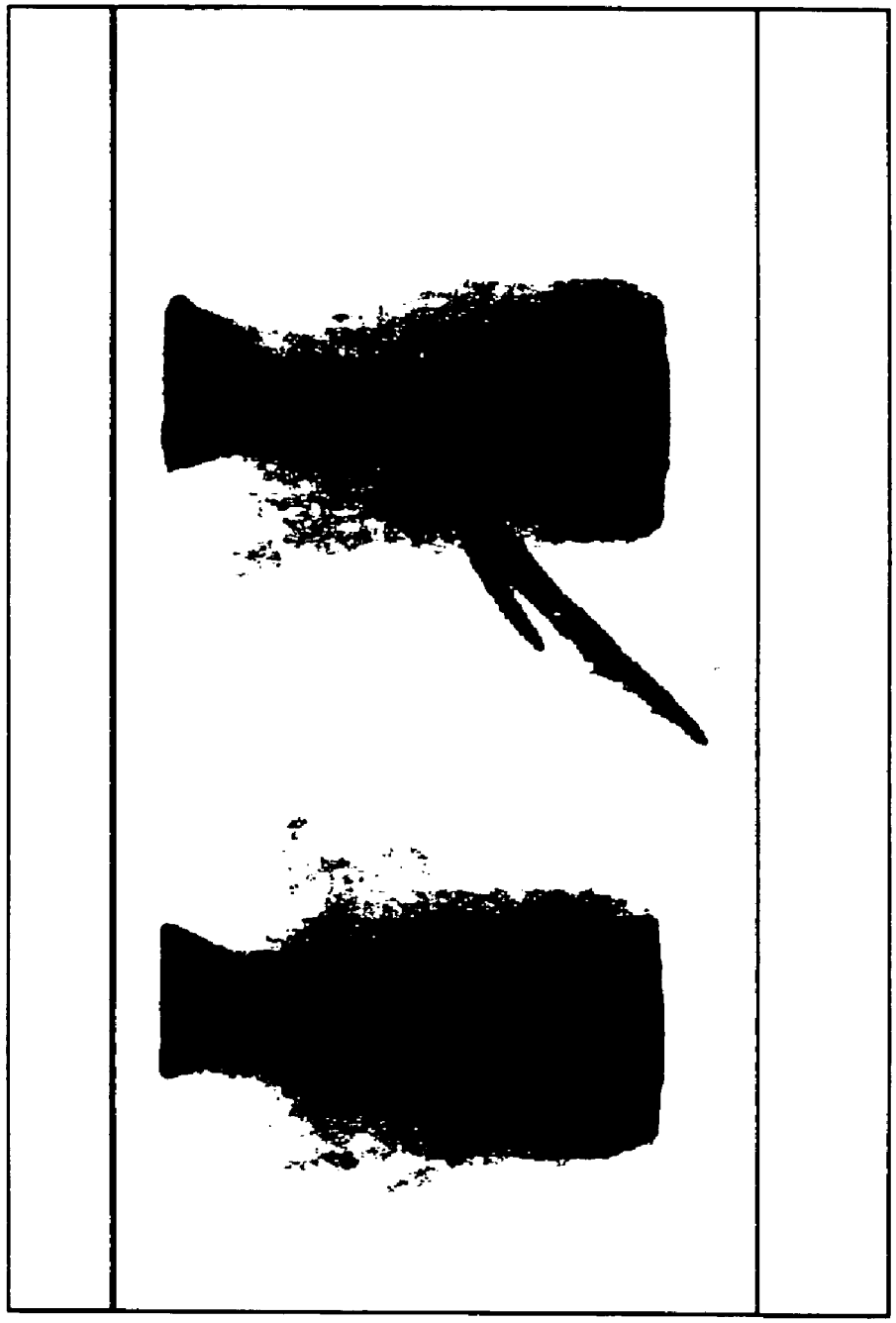
FIG. 7. $^{99m}$Tc-pertechnetate scintigraphy of a woman with a locally-advanced cancer of the right breast and an enlarged thyroid. The patient was scanned after injection of 15 mCi of $^{99m}$Tc-labeled pertechnetate ($^{99m}$TcO$_4^-$). Tracer accumulates in the thyroid and stomach. Tracer is present in the heart and liver due to vascular pooling. The arrow indicates distinct accumulation in the area of the breast cancer.

The results obtained from the studies on transgenic mice, and the similarity between the human breast cancer immunohistochemical patterns and those observed in thyroid cancer, indicate the likelihood that mgNIS expressed in human breast tumors is active. Clearly, the most direct way to determine the activity of mgNIS in breast cancer is to subject patients to scintigraphic evaluation with $^{99m}TcO_4^-$. One patient who was undergoing neoadjuvant hormonal therapy for locally-advanced breast cancer presented initially with an enlarged thyroid. Accordingly, she underwent whole-body $^{99m}TcO_4^-$ scanning. Significantly, the tracer was concentrated in the area of this patient's breast tumor (FIG. 7), which was a needle-biopsy-proven invasive ductal carcinoma (not shown). This is an extremely meaningful (if preliminary) finding that supports the notion that the use of radioiodide therapy as an adjuvant to surgical treatment of primary breast cancer, or as directed against systemic metastatic disease, may be highly effective.

REFERENCES

Amenta and Martinez-Hernandez, A Practical Approach. In *Extracellular Matrix Macromolecules*, 303-27, 1995.

Bale and Dorsa, Sex differences in and effects of estrogen on oxytocin receptor messenger ribonucleic acid expression in the ventral hypothalamus. *Endocrinology*, 136:27-32, 1995.

Bale and Dorsa, Cloning, novel promoter sequence and estrogen regulation of a rat oxytocin receptor gene. *Endocrinology*, 138:1151-58, 1997.

Cancroft and Goldsmith, $^{99m}$Tc-Pertechnetate scintigraphy as an aid in the diagnosis of breast masses. *Radiology*, 106:441-44, 1973.

Carrasco, N., Iodide transport in the thyroid gland. *Bioch. Biophys. Acta*, 1154:65-82, 1993.

Carrasco et al., Preparation of monoclonal antibodies against the lac permease of *Escherichia coli*. *Methods Enzymol.*, 125:453-67, 1986.

Dai et al., Cloning and characterization of the thyroid iodide transporter. *Nature*, 379:458-60, 1996a.

Dai et al., Transport Processes in Eukaryotic and Prokaryotic Organisms. In *Handbook of Biological Physics*, vol. 2 (Amsterdam: Elsevier, 1996b), 343-67.

DeGroot, L. J., In *Endocrinology* (Orlando, Fla.: Grune & Stratton Inc., 1989).

De la Vieja et al., Molecular analysis of the sodium/iodide symporter (NIS): Impact on thyroid and extrathyroid pathophysiology. *Phys. Rev.* (in press), 2000.

DiGiovanna, M. P., Clinical significance of HER-2/neu overexpression (Part I). *Principles and Practice of Oncology*, 13:1-10, 1999.

Dohan et al., Molecular study of the sodium-iodide symporter (NIS): A new field in thyroidology. *Trends in Endocrin. Metabol.* (in press), 2000.

Dorrington and Gore-Langton, Prolactin inhibits oestrogen synthesis in the ovary. *Nature*, 290:600-02, 1981.

Dorrington and Gore-Langton, Antigonadal action of prolactin: further studies on the mechanism of inhibition of follicle stimulating hormone induced aromatase activity in rat granulosa cell cultures. *Endocrinology*, 110:1701-07, 1982.

Dulbecco et al., Cell types and morphogenesis in the mammary gland. *Proc. Natl. Acad. Sci. USA*, 79:7346-50, 1982.

Eng et al., Escape from the acute Wolff-Chaikoff effect is associated with a decrease in thyroid sodium/iodide symporter messenger ribonucleic acid and protein. *Endocrinology*, 140:3404-10, 1999.

Eskandari et al., Thyroid Na$^+$/I$^-$ symporter: mechanism, stoichiometry, and specificity. *J. Biol. Chem.*, 272:27230-38, 1997.

Eskin, B. A., Iodine metabolism and breast cancer. *Trans. NY Acad. Sci.*, 32:911, 1970.

Fitzgibbons et al., Benign breast changes and subsequent risk for breast cancer. An update of the 1985 consensus statement. *Arch. Pathol. Lab. Med.*, 122:1053-55, 1998.

Fuchs et al., Correlation between oxytocin receptor concentration and responsiveness to oxytocin in pregnant rat myometrium: effects of ovarian steroids. *Endocrinology*, 113:742-49, 1983.

Fujiwara et al., Congenital hypothyroidism caused by a missense mutation in the Na$^+$/I$^-$ symporter. *Nature Gen.*, 16:124-25, 1997.

Gitay-Goren et al., Prolactin inhibits hCG-stimulated steroidogenesis and CAMP accumulation, possibly by increasing phosphodiesterase activity, in rat granulosa cell cultures. *Mol. Cell. Endocr.*, 61:69-76, 1989.

Grazzini et al., Inhibition of oxytocin receptor function by direct binding of progesterone. *Nature*, 392:509-12, 1998.

Greenlee et al., Cancer Statistics 2000. *A Cancer Journal for Clinicians*, 50:7-33, 2000.

Guy et al., Expression of the neu protooncogene in the mammary epithelium of transgenic mice induces metastatic disease. *Proc. Natl. Acad. Sci. USA*, 89:10578-82, 1992.

Harlow and Lane, Immunoblotting. In *Antibodies: a laboratory manual* (Cold Spring Harbor Laboratory, 1988), 471-506.

Helminen and Ericsson, Studies on mammary gland involution II. Ultrastructural evidence for auto- and heterophagocytosis. *J. Ultrastruct Res.*, 25:214-27, 1968.

Higushi et al., Release of oxytocin during suckling and parturition in rat. *J. Endocrinol.*, 105:339-46, 1985.

Hung and Lau, Basic science of HER-2/neu: a review *Sem. Oncol.*, 26:51-59, 1999.

Joshie et al., Cellular proliferation in the rat mammary gland during pregnancy and lactation, *Lab. Invest.*, 54:52-61, 1976.

Kaminsky et al., Na(+)-1-symport activity is present in membrane vesicles from thyrotropin-deprived non-I(-)-transporting cultured thyroid cells. *Proc. Natl. Acad. Sci. USA*, 91:3789-93, 1994.

Krasnow et al., Regulation of aromatase mRNA and estradiol biosynthesis in rat ovarian granulosa and luteal cells by prolactin. *Mol. Endocr.*, 4:13-21, 1990.

Larcher et al., Oxytocin receptor gene expression in the rat uterus during pregnancy and the estrus cycle and in response to gonadal steroid treatment. *Endocrinology*, 136:5350-56, 1994.

Levy et al., Characterization of the thyroid Na$^+$/I$^-$ symporter with an anti-COOH terminus antibody, *Proc. Natl. Acad. Sci. USA*, 94:5568-73, 1997.

Levy et al., N-linked glycosylation of the thyroid Na$^+$/I$^-$ Symporter (NIS): Implications for its secondary structure model. *J. Biol. Chem.*, 273:22657-63, 1998a.

Levy et al., Identification of a structural requirement for thyroid Na$^+$/I$^-$ symporter (NIS) function from analysis of a mutation that causes human congenital hypothyroidism. *FEBS Letters*, 429:36-40, 1998b.

Lyons et al., The hormonal control of mammary growth and lactation. *Recent Prog. Horm. Res.*, 14:219-48, 1958.

Ma et al., Negative regulatory element involved in the hormonal regulation of GlcNAc-1-P transferase gene in mouse mammary gland. *J. Biol. Chem.*, 271:11197-203, 1996.

Martinez-Hernandez et al., Removal of basement membrane in the involuting breast. *Lab. Invest.*, 34:455-62, 1976.

Mattheij et al., Intraperitoneal infusion of EDTA in the rat blocks completely the prolactin rise in the plasma during suckling. *Horm. Res.*, 16:219-29, 1982.

Matsuda and Kosugi, A homozygous missense mutation of the sodium/iodide symporter gene causing iodide transport defect. *J. Clin. Endocrin. Metab.*, 82:3966-71, 1997.

Mazzaferri, E. L., NCCN thyroid carcinoma practice guidelines. NCCN Proceedings. *Oncology*, 13:391-442, 1999.

McCormack and Greenwald, Progesterone and oestradiol-17-β concentrations in the peripheral plasma during pregnancy in the mouse. *J. Endocr.*, 62:101-07, 1974.

Mountford et al., Transfer of radioiodide to milk and its inhibition. *Nature*, 322:600, 1986.

Ohno et al., The paired domain transcription factor Pax8 binds to the upstream enhancer of the rat sodium/iodide symporter gene and participate in both thyroid-specific and cAMP dependent transcription. *Mol. Cell. Biol.*, 19:2051-60, 1997.

Papadopoulos et al., A comparison between the handling of iodine and technetium by the thyroid gland of the rat. *J. Endocrin.*, 38:381-87, 1967.

Paterson et al., Correlation between c-erbB-2 amplification and risk of recurrent disease in node-negative breast cancer. *Cancer Res.*, 51:556-67, 1991.

Rajput et al., Developmental and hormonal regulation of UDP-GlcNAc:Dolichol Phosphate GlcNAc-1-P transferase in mouse mammary gland. *J. Biol. Chem.*, 269: 16054-61, 1994.

Rosen, P. P., *Rosen's Breast Pathology* (Philadelphia: Lippincott-Raven, 1997), 209-321.

Rosenblatt et al., Hormonal basis during pregnancy for the onset of maternal behaviour in the rat. *Psychoneuroendocrinol.*, 13:29-46, 1988.

Siegel et al., Elevated expression of activated forms of neu/ErbB-2 and ErbB-3 are involved in the induction of mammary tumors in transgenic mice: implications for human breast cancer. *EMBO J.*, 18:2149-64, 1999.

Sinn et al., Co-expression of MMTV/V-Ha-ras and MMTV/c-myc genes in transgenic mice: synergistic actions of oncogenes in vivo. *Cell*, 49:465-75, 1987.

Slamon et al., Human breast cancer: correlation of relapse and survival with amplification of the HER-2/neu oncogene. *Science*, 235:177-82, 1987.

Smanik et al., Cloning of the human sodium iodide symporter. *Bioch. Biophys. Res. Comm.*, 226:339-45, 1996.

Spitzweg et al., Analysis of human sodium iodide symporter gene expression in extrathyroidal tissues and cloning of its complementary deoxyribonucleic acids from salivary gland, mammary gland, and gastric mucosa. *J. Clin. Endocrin. Metabol.*, 83:1746-51, 1998.

Sternberg, S. S., *Histology for Pathologists* (New York: Lippincott-Raven, 1997), 481-93.

Stubbe et al., Iodine deficiency and brain development. *Bibl. Nutr. Dieta*, 38:206-08, 1986.

Thorpe, S. M., Increased uptake of iodide by hormone-responsive compared to hormone-independent mammary tumors in GR mice. *Intl. J. Cancer*, 18:345-50, 1976.

Topper and Freeman, Multiple hormone interactions in the developmental biology of the mammary gland. *Physiol. Rev.*, 60:1049-106, 1981.

Umscheid et al., Up-regulation of oxytocin receptor messenger ribonucleic acid and protein by estradiol in the cervix of ovariectomized rat. *Biol. Reprod.*, 59:1131-38, 1998.

Villanueva et al., The prolactin inhibition of follicle-stimulating hormone-induced aromatase activity in cultured rat granulosa cells is in part tyrosine kinase and protein kinase-C dependent. *Mol. Hum. Reprod.*, 2:725-31, 1996.

Vonderhaar, B. K., Prolactin: transport, function and receptors in mammary gland development and differentiation. In *The Mammary Gland, Development, Regulation, Function* (New York: Plenum Press, 1987), 383-38.

Wakerley et al., Relationship between the suckling-induced release of oxytocin and prolactin in the urethane-anaesthetized lactating rat. *J. Endocrinology*, 76:493-500, 1978.

Werner and Ingbar, *The Thyroid: A Fundamental and Clinical Text* (Philadelphia: J. B. Lippincott, 1991), 1-1362.

Young et al., Deficiency in mouse oxytocin prevents milk ejection, but not fertility or parturition. *J. Neuroendocrinol.*, 8:847-53, 1996.

Zeng et al., Benign proliferative nipple duct lesions frequently contain CAM 5.2 and anti-cytokeratin 7 immunoreactive cells in the overlying epidermis. *Am. J. Surg. Pathol.*, 23:1349-55, 1999.

Zingg et al., Gonadal steroid regulation of oxytocin and oxytocin receptor gene expression. In *Oxytocin, Advances in Experimental Medicine and Biology* (New York: Plenum Press, 1995), 395-404.

Zingg et al., Genomic and non-genomic mechanisms of oxytocin receptor regulation. In *Vasopressin and Oxytocin, Advances in Experimental Medicine and Biology* (New York: Plenum Press, 1998), 287-97.

All publications mentioned hereinabove are hereby incorporated in their entirety. While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A method for assessing the efficacy of breast cancer therapy in a non-lactating human subject who has undergone or is undergoing treatment for breast cancer, comprising determining whether or not mammary gland sodium/iodide symporter (mgNIS) is expressed in breast tissue of the subject, wherein
   expression of mgNIS in the breast tissue is detected using an antibody, or a fragment thereof, specific for mgNIS, and
   expression of mgNIS in the breast tissue of the is indicative of the presence of breast cancer in the subject, and an absence of mgNIS expression in the breast tissue is indicative of successful breast cancer therapy in the subject.

2. The method of claim 1, wherein the expression of mgNIS is detected in vitro or in vivo.

3. The method of claim 1, wherein the antibody is labeled with a detectable marker.

4. A method for assessing the efficacy of breast cancer therapy in a non-lactating human subject who has undergone or is undergoing treatment for breast cancer, comprising determining whether or not mammary gland sodium/iodide symporter (mgNIS) is expressed in breast tissue of the subject, wherein
   expression of mgNIS in the breast tissue is detected in vitro using at least one nucleic acid probe that specifically hybridizes to nucleic acid encoding mgNIS, and
   expression of mgNIS in the breast tissue of the subject is indicative of the presence of breast cancer in the subject, and an absence of mgNIS expression in the breast tissue is indicative of successful breast cancer therapy in the subject.

5. The method of claim 4, wherein the nucleic acid probe is DNA.

6. The method of claim 4, wherein the nucleic acid probe is RNA.

7. The method of claim 4, wherein the nucleic acid probe is labeled with a detectable marker.

* * * * *